(12) United States Patent
Allen et al.

(10) Patent No.: US 8,828,009 B2
(45) Date of Patent: Sep. 9, 2014

(54) IMPLANTS, SURGICAL METHODS, AND INSTRUMENTATION FOR USE IN FEMOROACETABULAR IMPINGEMENT SURGERIES

(75) Inventors: Charles Wayne Allen, Southaven, MS (US); David Wayne Rister, Hernando, MS (US); Phillip E. Frederick, Memphis, TN (US); Kevin Wayne Belew, Hernando, MS (US); Lauren Christina Jasper, Memphis, TN (US); James Curtis Gatewood, Memphis, MS (US); Kevin Ray Hays, Somerville, TN (US)

(73) Assignee: Smith & Nephew, Inc., Cordova, TN (US)

( * ) Notice: Subject to any disclaimer, the term of this patent is extended or adjusted under 35 U.S.C. 154(b) by 335 days.

(21) Appl. No.: 13/217,970

(22) Filed: Aug. 25, 2011

(65) Prior Publication Data

US 2012/0053590 A1 Mar. 1, 2012

Related U.S. Application Data

(60) Provisional application No. 61/402,249, filed on Aug. 26, 2010.

(51) Int. Cl.
*A61F 5/00* (2006.01)
*A61B 17/17* (2006.01)
*A61F 2/30* (2006.01)
*A61F 2/34* (2006.01)
*A61F 2/46* (2006.01)

(52) U.S. Cl.
CPC ........... *A61F 2/34* (2013.01); *A61F 2002/3038* (2013.01); *A61F 2002/30731* (2013.01); *A61F 2002/3487* (2013.01); *A61B 17/1746* (2013.01); *A61F 2002/30387* (2013.01); *A61F 2002/30578* (2013.01); *A61F 2002/30589* (2013.01); *A61F 2002/3085* (2013.01); *A61F 2002/30971* (2013.01); *A61F 2002/305* (2013.01); *A61F 2/30749* (2013.01); *A61F 2002/4631* (2013.01); *A61F 2/30756* (2013.01); *A61F 2002/30448* (2013.01); *A61F 2/30728* (2013.01)
USPC ............................................................ 606/87

(58) Field of Classification Search
USPC ............................................................ 606/87
See application file for complete search history.

(56) References Cited

U.S. PATENT DOCUMENTS

| 2,691,979 A | 10/1954 | Watson |
| 4,851,006 A | 7/1989 | Tuke |

(Continued)

FOREIGN PATENT DOCUMENTS

| AU | 2006334522 | 7/2007 |
| AU | 2008260279 | 12/2008 |

(Continued)

OTHER PUBLICATIONS

International Search Report and Written Opinion dated Mar. 27, 2012 in Application No. PCT/US2011/049129.

(Continued)

*Primary Examiner* — Nicholas Woodall
(74) *Attorney, Agent, or Firm* — James L. Ewing, IV; Michael A. Bertelson; Kilpatrick Townsend & Stockton LLP

(57) ABSTRACT

Implants, surgical methods, and instrumentation for treating femoroacetabular impingement. In some embodiments, implants are provided or formed on the acetabulum to replicate the anatomy of the acetabulum (e.g., the acetabular rim and/or labrum, the bearing surface in the acetabulum, cartilage in the acetabulum, etc.). Also provided are embodiments of materials and instruments for use in installing and/or forming such implants on the acetabulum. Further provided are embodiments of guide jigs for use in preparing the acetabulum to receive such implants.

18 Claims, 23 Drawing Sheets

(56) References Cited

U.S. PATENT DOCUMENTS

| | | |
|---|---|---|
| 4,955,919 A | 9/1990 | Pappas et al. |
| 4,959,072 A | 9/1990 | Morscher et al. |
| 5,047,062 A | 9/1991 | Pappas et al. |
| 5,127,920 A | 7/1992 | MacArthur |
| 5,133,764 A | 7/1992 | Pappas et al. |
| 5,376,122 A | 12/1994 | Pappas et al. |
| 5,376,125 A | 12/1994 | Winkler et al. |
| 5,879,404 A | 3/1999 | Bateman et al. |
| 5,880,976 A | 3/1999 | DiGioia III et al. |
| 5,913,899 A | 6/1999 | Barrett et al. |
| 5,995,738 A | 11/1999 | DiGioia, III et al. |
| 6,002,859 A | 12/1999 | DiGioia, III et al. |
| 6,120,546 A | 9/2000 | Dye et al. |
| 6,136,034 A | 10/2000 | Townley |
| 6,162,257 A | 12/2000 | Gustilo et al. |
| 6,200,350 B1 | 3/2001 | Masini |
| 6,205,411 B1 | 3/2001 | DiGioia, III et al. |
| 6,299,647 B1 | 10/2001 | Townley |
| 6,383,224 B1 | 5/2002 | Gie et al. |
| 6,383,225 B2 | 5/2002 | Masini |
| 6,475,243 B1 | 11/2002 | Sheldon et al. |
| 6,695,883 B2 | 2/2004 | Crofford |
| 6,783,553 B2 | 8/2004 | Grimes |
| 6,923,833 B2 | 8/2005 | Wasielewski |
| 7,022,142 B2 | 4/2006 | Johnson |
| 7,060,102 B2 | 6/2006 | Thompson et al. |
| 7,074,241 B2 | 7/2006 | McKinnon |
| 7,104,995 B2 | 9/2006 | Crofford |
| 7,115,145 B2 | 10/2006 | Richards |
| 7,169,186 B2 | 1/2007 | Harris et al. |
| 7,291,176 B2 | 11/2007 | Serra et al. |
| 7,611,541 B2 | 11/2009 | Thompson et al. |
| 7,615,083 B2 | 11/2009 | Wasielewski |
| 7,682,398 B2 | 3/2010 | Croxton et al. |
| 7,695,474 B2 | 4/2010 | Crofford |
| 7,708,783 B2 | 5/2010 | Richards |
| 2001/0001121 A1 | 5/2001 | Lombardo et al. |
| 2002/0128653 A1 | 9/2002 | Haidukewych |
| 2002/0128720 A1 | 9/2002 | Masini |
| 2003/0187513 A1 | 10/2003 | Durniak |
| 2003/0212458 A1 | 11/2003 | Harris et al. |
| 2003/0212459 A1 | 11/2003 | Gibbs |
| 2004/0083004 A1 | 4/2004 | Wasielewski |
| 2004/0133979 A1 | 7/2004 | Newkirk et al. |
| 2004/0138757 A1 | 7/2004 | Nadzadi et al. |
| 2004/0153062 A1 | 8/2004 | McGinley et al. |
| 2004/0162621 A1 | 8/2004 | Crofford |
| 2004/0236341 A1 | 11/2004 | Petersen |
| 2005/0010232 A1 | 1/2005 | Crofford |
| 2005/0049714 A1 | 3/2005 | Crofford |
| 2005/0182493 A1 | 8/2005 | Bertram, III |
| 2005/0182496 A1 | 8/2005 | Hunter et al. |
| 2005/0203384 A1 | 9/2005 | Sati et al. |
| 2005/0245934 A1 | 11/2005 | Tuke et al. |
| 2006/0161167 A1 | 7/2006 | Myers et al. |
| 2006/0241780 A1 | 10/2006 | McKinnon |
| 2006/0264731 A1 | 11/2006 | Murphy |
| 2006/0293682 A1 | 12/2006 | Justin et al. |
| 2007/0032878 A1 | 2/2007 | Bader et al. |
| 2007/0083214 A1 | 4/2007 | Duncan et al. |
| 2007/0135927 A1 | 6/2007 | Harris et al. |
| 2007/0161935 A1 | 7/2007 | Torrie et al. |
| 2007/0198022 A1 | 8/2007 | Lang et al. |
| 2007/0225818 A1 | 9/2007 | Reubelt et al. |
| 2007/0227024 A1 | 10/2007 | Beaule |
| 2007/0249967 A1 | 10/2007 | Buly et al. |
| 2007/0260256 A1 | 11/2007 | Beaule |
| 2007/0265635 A1 | 11/2007 | Torrie et al. |
| 2007/0299452 A1 | 12/2007 | Curry |
| 2008/0195221 A1 | 8/2008 | Howald et al. |
| 2008/0208200 A1 | 8/2008 | Crofford |
| 2008/0225818 A1 | 9/2008 | Niu et al. |
| 2008/0234685 A1 | 9/2008 | Gjerde |
| 2008/0243127 A1 | 10/2008 | Lang et al. |
| 2008/0281328 A1 | 11/2008 | Lang et al. |
| 2008/0281329 A1 | 11/2008 | Fitz et al. |
| 2008/0281426 A1 | 11/2008 | Fitz et al. |
| 2009/0069845 A1 | 3/2009 | Frushell et al. |
| 2009/0099570 A1 | 4/2009 | Paradis et al. |
| 2009/0112214 A1 | 4/2009 | Philippon et al. |
| 2009/0131956 A1 | 5/2009 | Dewey et al. |
| 2009/0149965 A1 | 6/2009 | Quald |
| 2009/0182340 A1 | 7/2009 | Nikolchev et al. |
| 2009/0192620 A1 | 7/2009 | Ebbitt |
| 2009/0198274 A1 | 8/2009 | Frushell et al. |
| 2009/0216113 A1 | 8/2009 | Meier et al. |
| 2009/0289806 A1 | 11/2009 | Thornberry |
| 2009/0306586 A1 | 12/2009 | Ross et al. |
| 2009/0316967 A1 | 12/2009 | Dardenne et al. |
| 2010/0016892 A1 | 1/2010 | Kaiser et al. |
| 2010/0086186 A1 | 4/2010 | Zug et al. |
| 2010/0114101 A1 | 5/2010 | Crofford |
| 2010/0152859 A1 | 6/2010 | Thompson et al. |
| 2012/0283840 A1 | 11/2012 | Frederick et al. |

FOREIGN PATENT DOCUMENTS

| | | |
|---|---|---|
| CH | 449174 | 12/1967 |
| EP | 0289192 | 11/1988 |
| EP | 0803234 | 10/1997 |
| EP | 1195149 | 4/2002 |
| EP | 1437987 | 7/2004 |
| EP | 1472997 | 11/2004 |
| EP | 1472998 | 11/2004 |
| EP | 1263350 | 1/2005 |
| EP | 1493406 | 1/2005 |
| EP | 1506749 | 2/2005 |
| EP | 1520559 | 4/2005 |
| EP | 1550024 | 7/2005 |
| EP | 1553898 | 7/2005 |
| EP | 1673043 | 6/2006 |
| EP | 1494625 | 8/2006 |
| EP | 1713420 | 10/2006 |
| EP | 1304980 | 5/2007 |
| EP | 1945146 | 7/2008 |
| EP | 1954235 | 8/2008 |
| EP | 1981409 | 10/2008 |
| EP | 1996123 | 12/2008 |
| EP | 1628590 | 4/2009 |
| EP | 2124764 | 12/2009 |
| EP | 2152219 | 2/2010 |
| EP | 1499268 | 4/2010 |
| EP | 2175419 | 4/2010 |
| EP | 2185108 | 5/2010 |
| GB | 2139098 | 11/1984 |
| JP | 2009525767 | 7/2009 |
| WO | WO88/07356 | 10/1988 |
| WO | WO01/67999 | 9/2001 |
| WO | WO02/09615 | 2/2002 |
| WO | WO02/09616 | 2/2002 |
| WO | WO03/034952 | 5/2003 |
| WO | WO03/086242 | 10/2003 |
| WO | WO03/086243 | 10/2003 |
| WO | WO03/094802 | 11/2003 |
| WO | WO04/001569 | 12/2003 |
| WO | WO2004/037129 | 5/2004 |
| WO | WO2005/000140 | 1/2005 |
| WO | WO2005/039453 | 5/2005 |
| WO | WO2005/072231 | 8/2005 |
| WO | WO2006/030392 | 3/2006 |
| WO | WO2007/021806 | 2/2007 |
| WO | WO2007/056678 | 5/2007 |
| WO | WO2007/080454 | 7/2007 |
| WO | WO2007/092841 | 8/2007 |
| WO | WO2007/109291 | 9/2007 |
| WO | WO2008/090468 | 7/2008 |
| WO | WO2008/112996 | 9/2008 |
| WO | WO2008/130656 | 10/2008 |
| WO | WO2008/150731 | 12/2008 |
| WO | WO2009/039513 | 3/2009 |
| WO | WO2009/046547 | 4/2009 |
| WO | WO2009/058830 | 5/2009 |
| WO | WO2009/076293 | 6/2009 |
| WO | WO2009/076297 | 6/2009 |

(56) References Cited

FOREIGN PATENT DOCUMENTS

| WO | WO2009/108683 | 9/2009 |
|---|---|---|
| WO | WO2009/114829 | 9/2009 |
| WO | WO2010/033473 | 3/2010 |
| WO | WO2010/052500 | 5/2010 |
| WO | WO2010/065901 | 6/2010 |
| WO | WO2010/096124 | 8/2010 |
| WO | WO2010/099247 | 9/2010 |

OTHER PUBLICATIONS

International Preliminary Report on Patentability dated Mar. 7, 2013 in Application No. PCT/US2011/049129.
International Search Report for PCT/US2009/056890, mailed Apr. 5, 2010.
International Preliminary Report on Patentability and Written Opinion for PCT/US2009/056890, mailed Mar. 22, 2011.
International Search Report and Written Opinion for PCT/US2010/025292, mailed Dec. 28, 2010.
International Preliminary Report on Patentability and Written Opinion for PCT/US2010/025292, mailed Aug. 30, 2011.
International Search Report for PCT/IB2006/004038, mailed Aug. 29, 2007.
Byrd, et al., "Arthroscopic Management of Femoracetabular Impingement," AAOS Instructure Course Lectures, vol. 58, 2009, pp. 231-239.
Leunig, et al., "Femoracetabular Impingement: Etiology and Surgical Concept," Operative Techniques in Orthopaedics, Jun. 5, 2005, pp. 247-255.
Leunig, et al. "Femoracetabular Impingement: Treatment of the Acetabular Side," AAOS Instructional Course Lectures, vol. 58, 2009, pp. 223-229.

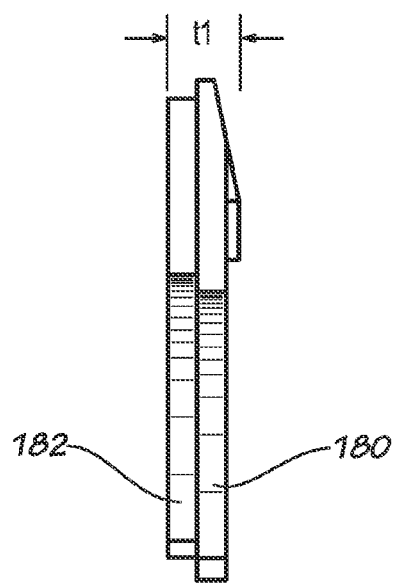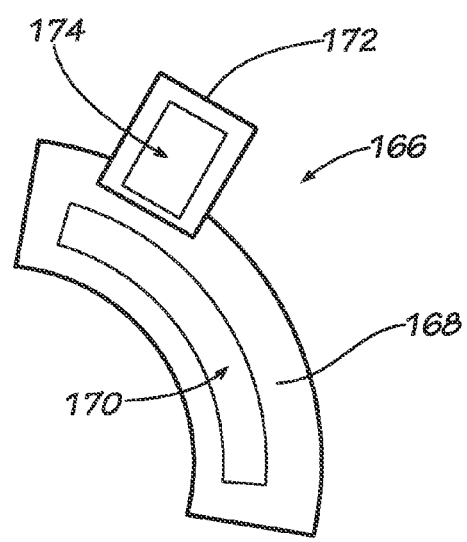
FIG. 23A  FIG. 23B
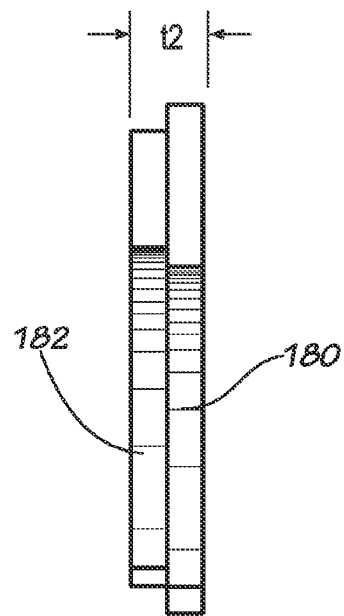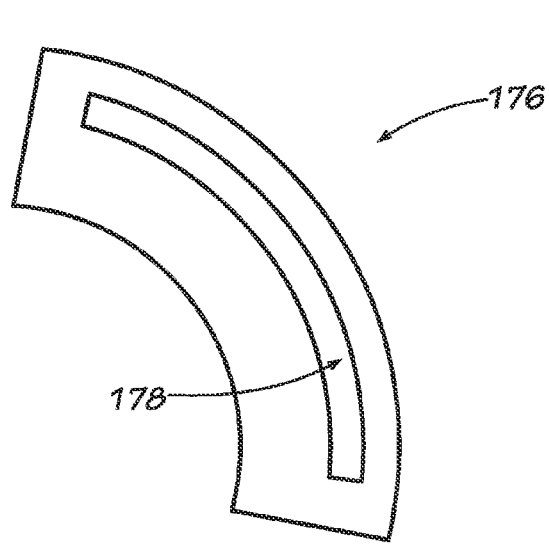
FIG. 24A  FIG. 24B

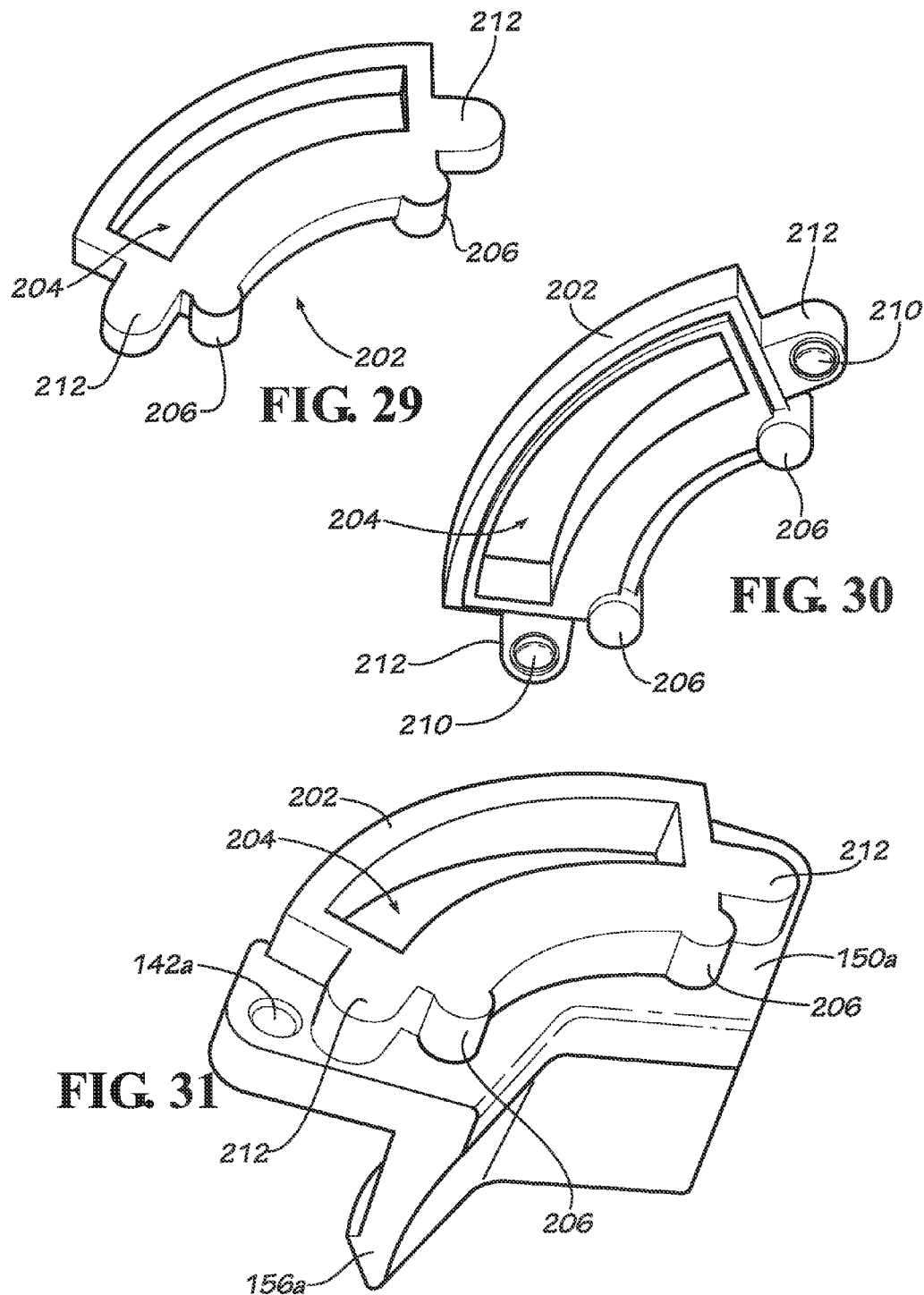

ance ex US 8,828,009 B2

IMPLANTS, SURGICAL METHODS, AND INSTRUMENTATION FOR USE IN FEMOROACETABULAR IMPINGEMENT SURGERIES

CROSS-REFERENCE TO RELATED APPLICATIONS

This application claims the benefit of U.S. Provisional Application No. 61/402,249, filed Aug. 26, 2010, the entire contents of which are herein incorporated by reference.

FIELD

This invention relates generally to hip surgeries and, more particularly, relates to implants, surgical methods, and instrumentation for treating femoroacetabular impingement.

BACKGROUND

Femoroacetabular impingement (or FAI) is a condition of the hip joint where the femoral head and acetabulum rub abnormally, thus creating damage to the hip joint. The damage can occur to the articular cartilage of the femoral head or acetabulum, or to the labral cartilage on and around the acetabular rim. Increasingly, FAI is being recognized as a cause of significant hip pain and disability and is implicated as a cause of secondary osteoarthritis.

FAI may take one of two forms: cam or pincer. The difference between the two forms is determined by the abnormality of the hip joint that is the cause of the damage. The cam form of FAI occurs when the femoral head and neck relationship is aspherical, or not perfectly round. This loss of roundness contributes to abnormal contact between the femoral head and the acetabulum. It may also cause damage to the acetabular labrum, the peripheral cartilage that surrounds a portion of the acetabular rim. The pincer form of FAI occurs when the acetabulum has too much coverage of the femoral head. This over-coverage typically exists along the front-top rim of the acetabulum and results in the acetabular labrum and/or marginal articular cartilage being "pinched" between the acetabular rim and the neck of the femur. The cam and pincer forms of FAI may exist together (thus creating a compound form of FAI).

Cam or pincer FAI is commonly associated with other maladies to the bone and/or cartilage. For example, in some cases a portion of the acetabulum may contain a lesion. Contact between the femoral head and the lesioned portion of the acetabulum might create pain and discomfort in the patient. Damage to the patient's cartilage is often common with FAI—either the cartilage of the femoral head, the acetabulum, or the acetabular labrum. Patients with extensive FAI may experience tears of the cartilage due to excessive contact between the acetabulum and the femoral head. Damage to the cartilage may extend into the acetabulum.

Known treatments of FAI include surgical intervention to debride affected cartilage, combined with the use of osteotomy to reshape irregular bone (on either the femoral head or the acetabulum). For example, to treat cam-type FAI, osteotomy may be used to reshape the femoral head to be more spherical. For pincer-type FAI, osteotomy may be used in or around the acetabulum to trim any excessive coverage of the femoral head. The known treatments include "open surgery," arthroscopy, or a combination of the two. In open surgery, the hip is dislocated through an incision of approximately 6 to 10 inches. Open surgery presents a high risk of blood loss and heightened recovery time. Arthroscopy may involve anywhere between two to four incisions, each of approximately 1 cm in length. The leg is placed in traction (in some cases, up to 50 lbs) to separate the hip joint and to make room for surgical instruments. Improper use of traction may cause nerve damage that may or may not heal with time. Additionally, arthroscopy presents poor visualization for the surgeon and requires significant training to become proficient. Finally, not all forms of FAI can be treated using arthroscopy. In combined surgery (also known as limited or "mini open" surgery), arthroscopy is used to repair acetabular labrum and cartilage, and a larger incision is made so that the surgeon may use osteotomy to reshape irregular bone.

These known treatments of FAI are limited to removing the patient's tissue: either debridement of soft tissue or osteotomy on the bone. The treatments are relatively new, and thus, long-term effects of the treatments are unknown. There is a concern that removing or reshaping the bone is not an effective long-term solution because the bone might grow back, thus requiring additional surgeries. Additionally, in these known treatments the cartilage and/or acetabular labrum are completely removed in order to obtain access to (and trim or reshape) the bone. No steps are taken to replace the removed tissue. Thus, after the patient's initial recovery from the surgery, the patient might experience pain due to the loss of the cartilage and acetabular labrum. For example, the patient would lose the "shock absorption" provided by these materials, and might experience pain due to bone-on-bone contact between the femoral head and the acetabulum. Additional surgeries may be required to address any issues caused by the loss of cartilage and/or regrowth of the bone. Finally, osteotomy on the bone might not be effective if the bone is irregularly shaped in that it has a depression (rather than a protruding portion of bone) or if the bone has a lesion. For example, although protruding portions of bone might be trimmed and reshaped easily, depressions cannot be reshaped because in a depression, there is little to no material to remove. Thus, the use of osteotomy on the bone may present several problems.

More recent developments involve the use of implants to replace and replicate the function of anatomy of the acetabulum and in particular the labrum, acetabular rim, and/or acetabular bearing surface. WO 2010/099247, the entirety of which is herein incorporated by reference, describes a variety of implants that may be positioned and fixed on the acetabulum to replace damaged cartilage (e.g., the labrum) and bone. FIG. 1 illustrates an embodiment of such an implant positioned on an acetabular rim 1004 in the acetabulum 1002 of a pelvic bone 1000. The implant 10 includes a rim portion 16 (which includes ridge 15) to replicate the acetabular rim and labrum and thereby capture the head of the femur within the acetabulum. The implant 10 also includes a bearing surface 18 that can generally align with the bearing surface 1006 of the acetabulum to provide a continuous surface on which the femoral head can articulate. The implant 10 wraps around at least a portion of the acetabular rim 1004.

In other embodiments, such as shown in FIGS. 2A-F, tools may be used to create prepared bone surfaces 1010, 1011 in a portion of the acetabulum 1002 and/or acetabular rim 1004. The prepared bone surfaces 1010, 1011 may have roughly the same shape as the implant 10, such that the implant 10 fits onto the prepared bone surfaces 1010, 1011. The implants 10 can have varying geometries and can be provided with mounting holes 20 to secure the implant 10 to the acetabulum 1002 and/or acetabular rim 1004 with fasteners.

SUMMARY

Embodiments disclosed herein are directed to implants, surgical methods, and instrumentation for treating femoroacetabular impingement. In some embodiments, implants are provided or formed on the acetabulum to replicate the anatomy of the acetabulum (e.g., the acteabular rim and/or labrum, the bearing surface in the acetabulum, cartilage in the acetablum, etc.). Also provided are embodiments of materials and instruments for use in installing and/or forming such implants on the acetabulum. Further provided are embodiments of guide jigs for use in preparing the acetabulum to receive such implants.

Further features and advantages of at least some of the embodiments of the present invention, as well as the structure and operation of various embodiments of the present invention, are described in detail below with reference to the accompanying drawings.

BRIEF DESCRIPTION OF THE DRAWINGS

A full and enabling disclosure directed to one of ordinary skill in the art is set forth more particularly in the remainder of the specification. The specification makes reference to the following appended figures, in which use of like reference numerals in different features is intended to illustrate like or analogous components.

FIG. 23A-B illustrate one embodiment of a cutting insert for use with the guide jig of FIGS. 22A-E.

FIG. 24A-B illustrate another embodiment of a cutting insert for use with the guide jig of FIGS. 22A-E.

FIG. 29 is a top perspective view of a cutting insert according to another embodiment.

FIG. 30 is a bottom perspective view of the cutting insert of FIG. 29.

FIG. 31 is a top perspective view of the cutting insert of FIGS. 29 and 30 mounted on the guide jig of FIG. 28.

DETAILED DESCRIPTION OF THE DRAWINGS

Figure 1:
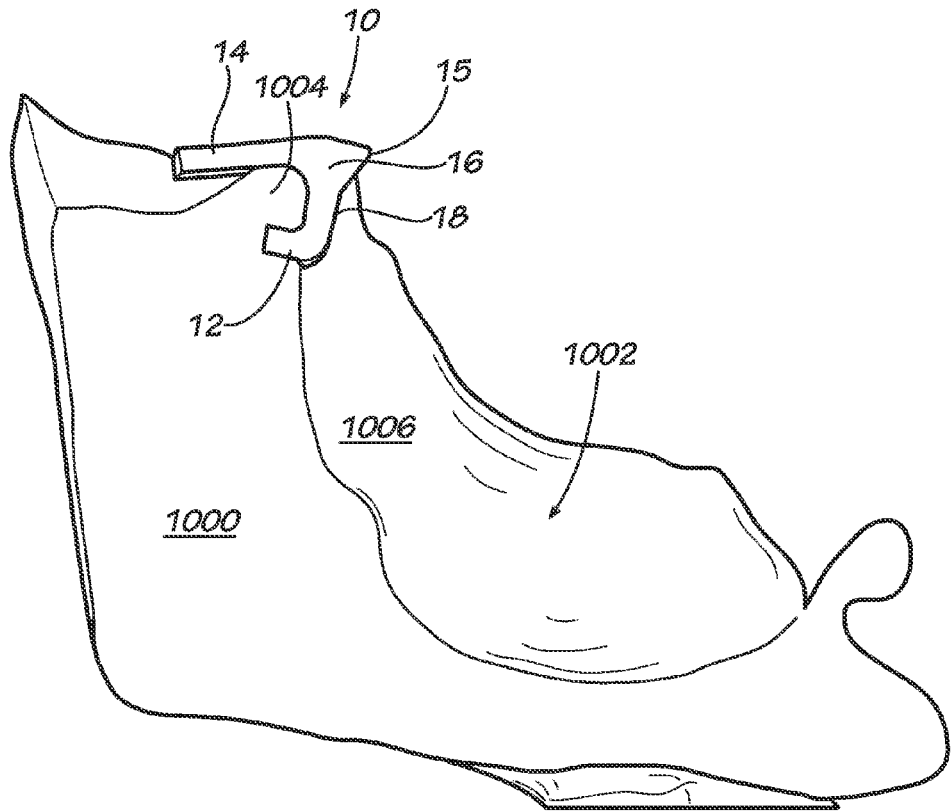
FIG. 1 is a partial cross-sectional view of an acetabular implant positioned on an acetabular rim.

The subject matter of embodiments of the present invention is described here with specificity to meet statutory requirements, but this description is not necessarily intended to limit the scope of the claims. The claimed subject matter may be embodied in other ways, may include different elements or steps, and may be used in conjunction with other existing or future technologies. This description should not be interpreted as implying any particular order or arrangement among or between various steps or elements except when the order of individual steps or arrangement of elements is explicitly described.

FIGS. 3-6 illustrate an acetabular implant 50 according to certain embodiments. The acetabular implant 50 includes a rim portion 12 having a bearing surface 18 and a flange portion 14. As best seen in FIG. 7C, when positioned on the prepared bone surfaces 1010, 1011 of the acetabulum 1002, the rim portion 12 extends along the bearing surface 1006 of the acetabulum 1002 and wraps around the acetabular rim 1004. The flange portion 14 extends from the rim portion 12 away from the acetabulum 1002. In this disclosed embodiment, flange portion 14 includes mounting holes 20 that receive anchors (not shown) to fix the implant 50 to the bone. It should be understood that mounting holes 20 are only optional and are in no way limiting.

It may be desirable to provide additional fixation along the rim portion 12 where the femoral head contacts and rubs against the bearing surface 18 of the implant 50, thus applying torque to the implant 50. In some embodiments, an anchor slot 52 may be provided on the rear surface 13 (opposite the bearing surface 18) of the rim portion 12. The anchor slot 52 does not extend through the thickness of the rim portion 12. The anchor slot 52 is designed to receive anchor(s) 60 that are inserted in the prepared bone surface 1010, thus securing the implant 50 to bone. For convenience, "anchor" is used generically to refer to screws, nails, fasteners, bone anchors, pins, pegs, K-wires, etc., and it should be understood that phrase is in no way limiting.

Figure 6:
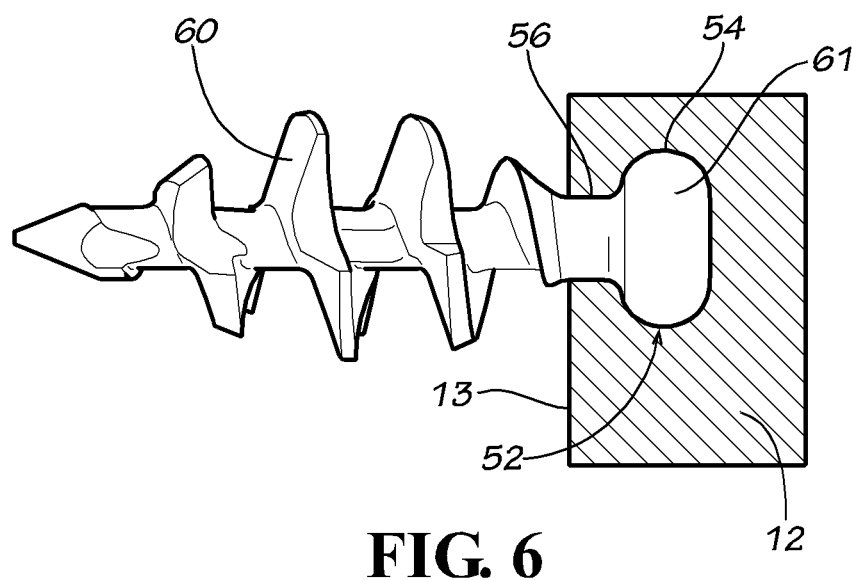
FIG. 6 is a partial cross-sectional view of an anchor positioned in the acetabular implant of FIG. 3 or FIG. 5.

As shown in FIG. 6, in certain embodiments the anchor slot 52 has an undercut portion 54 that is dimensioned to receive the head 61 of an anchor 60, and a neck 56 to retain the head 61 within the anchor slot 52.

Figure 3:
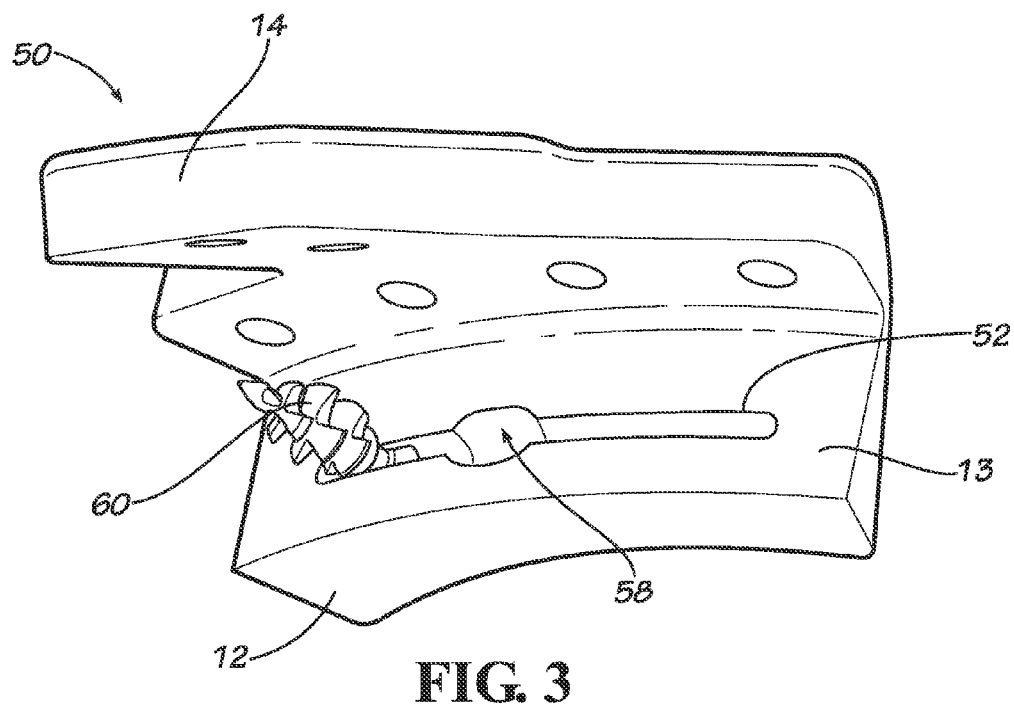
FIG. 3 is a bottom perspective view of another embodiment of an acetabular implant.
Figure 4A:
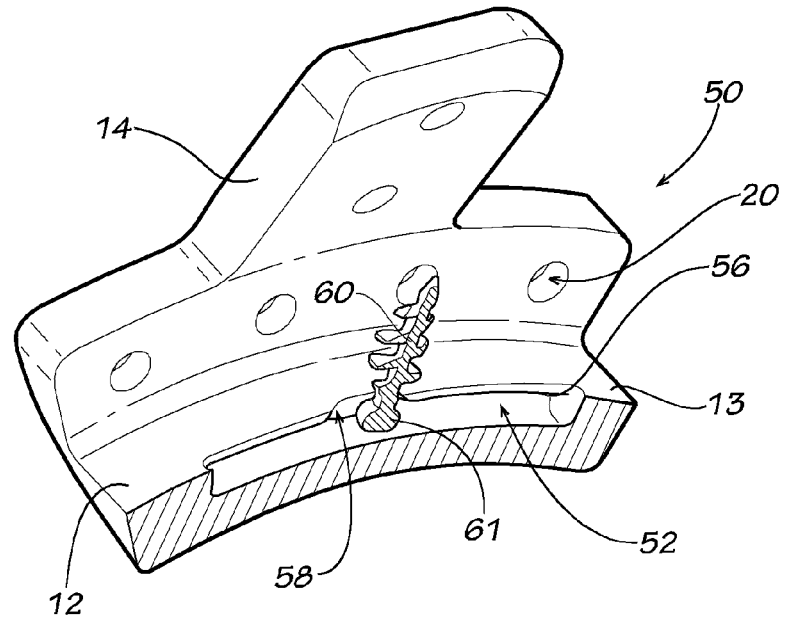
FIGS. 4A-B are partial cross-sectional views of the acetabular implant of FIG. 3.
Figure 4B:
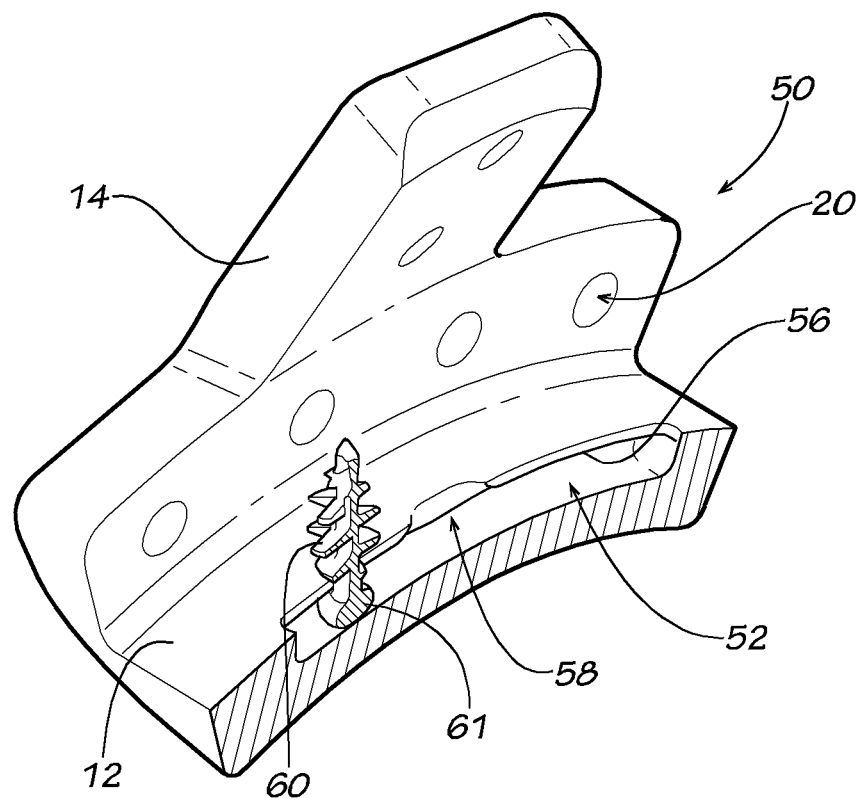

In some embodiments, the neck 56 does not extend along the entire length of the anchor slot 52 so as to create at least one opening 58 along the anchor slot 52 (see FIG. 3). Thus, the head 61 of an anchor 60 may be inserted into the anchor slot 52 at the opening 58, as seen in FIG. 4A. By translating or sliding the anchor 60 along the anchor slot 52 (see FIG. 4B), the head 61 of the anchor 60 is captured behind neck 56, which thereby prevents disengagement of the anchor 60 from anchor slot 52.

Figure 5:
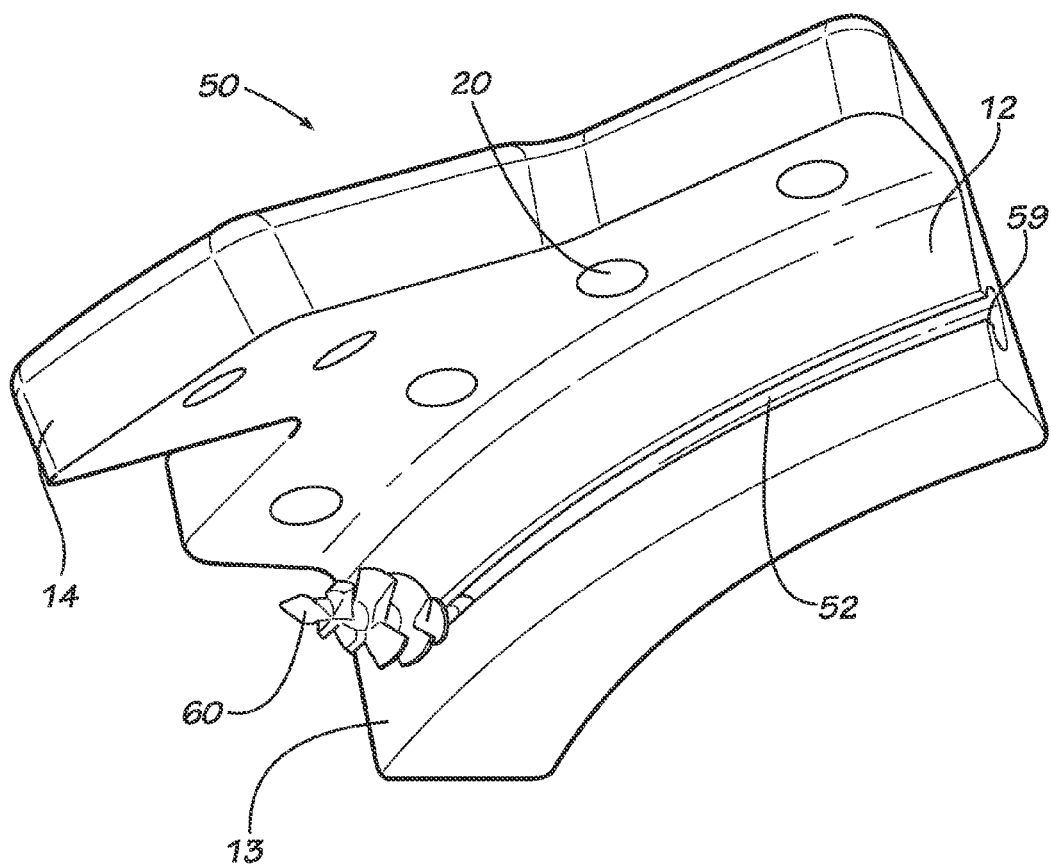
FIG. 5 is a bottom perspective view of yet another embodiment of an acetabular implant.

In other embodiments, the anchor slot 52 extends all the way to an edge of the implant 50 so as to have an opening 59 along the edge of the implant 50, as illustrated in FIG. 5. In such embodiments, an opening 58 need not be provided along the anchor slot 52 and the anchor 60 engages the slot via opening 59 along the edge of the implant 50. In some embodiments, implant 50 is provided with both opening 59 and opening 59 to impart multiple means of ingress and egress for an anchor 60.

While certainly not required, if desired the cross-sectional shape of the anchor slot 52 (i.e., the undercut portion 54 and the neck 56) may be dimensioned to approximate the cross-sectional shape of the head 61 of anchor 60. This results in minimal clearance between the head 61 of the anchor 60 and the anchor slot 52, which may minimize loosening of the implant 50 with respect to the bone. In other embodiments more or less clearance may be provided. The anchor slot 52 may be sized to retain any number of anchors 60. Moreover, more than one opening 58 may be provided along an anchor slot 52.

Figure 7A:
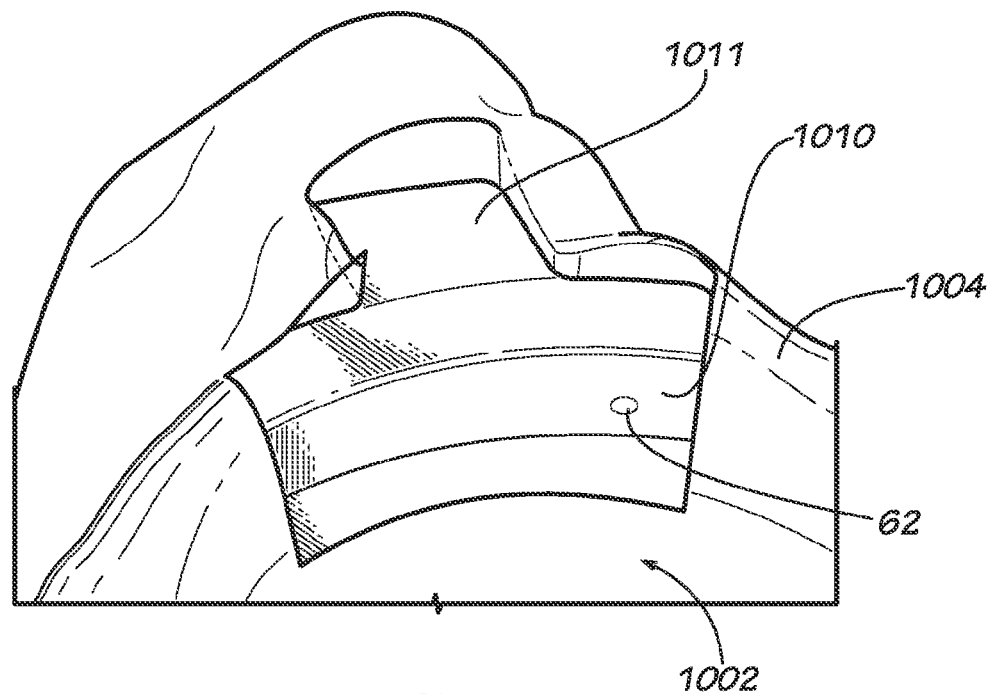
FIG. 7A-C illustrate methods of attaching the acetabular implant of FIG. 3 to an acetabulum.

There are several ways that implants 50 having anchor slots 52 may be installed on the bone. In one method, as shown in FIG. 7A, prepared bone surfaces 1010, 1011 are cut into the acetabulum 1002 and/or rim 1004 to receive the desired implant. Next, a hole 62 is drilled into the prepared bone surface 1010 to receive each anchor 60. Note that any number of anchors 60 may be used.

Figure 7B:
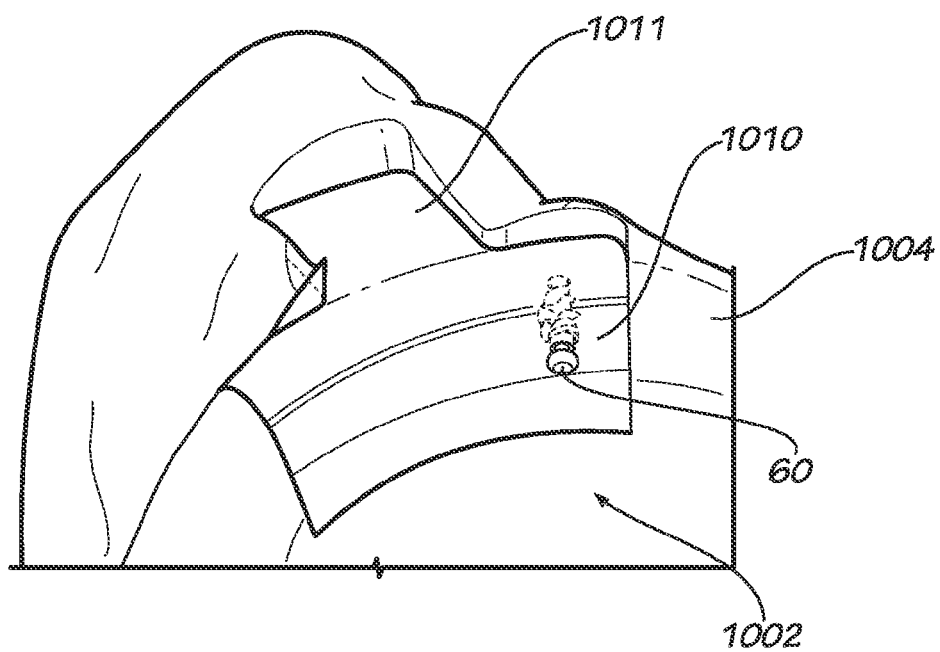
Figure 7C:
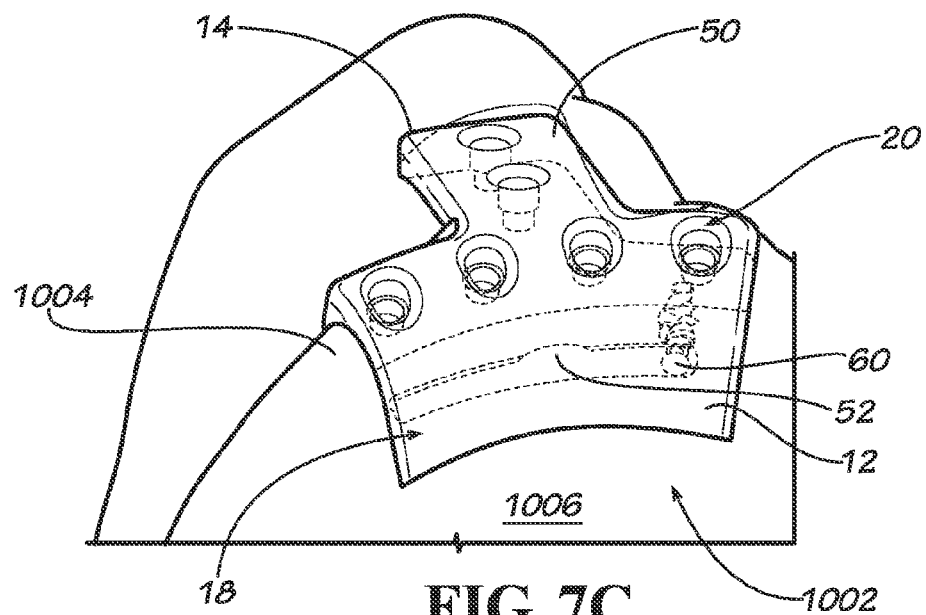
Figure 8A:
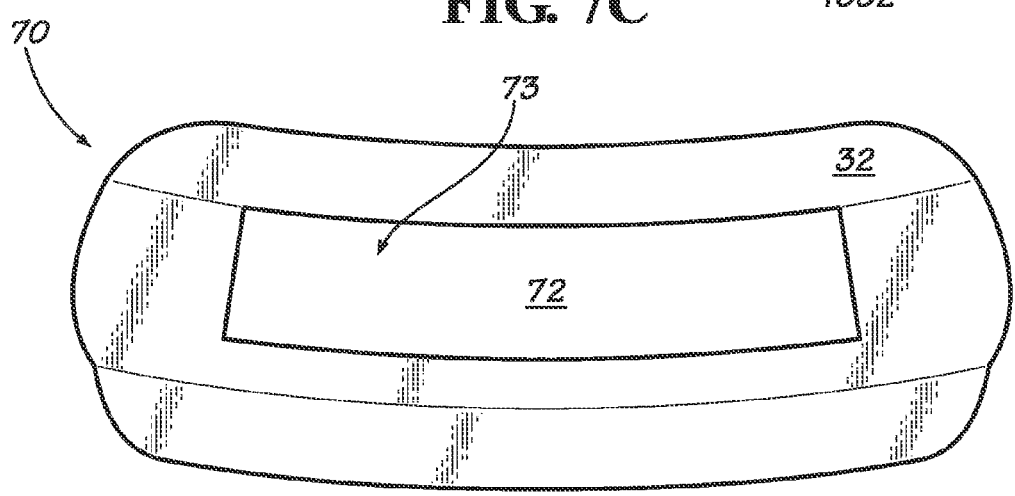
FIGS. 8A-C are various views of an acetabular implant according to another embodiment.
Figure 8B:
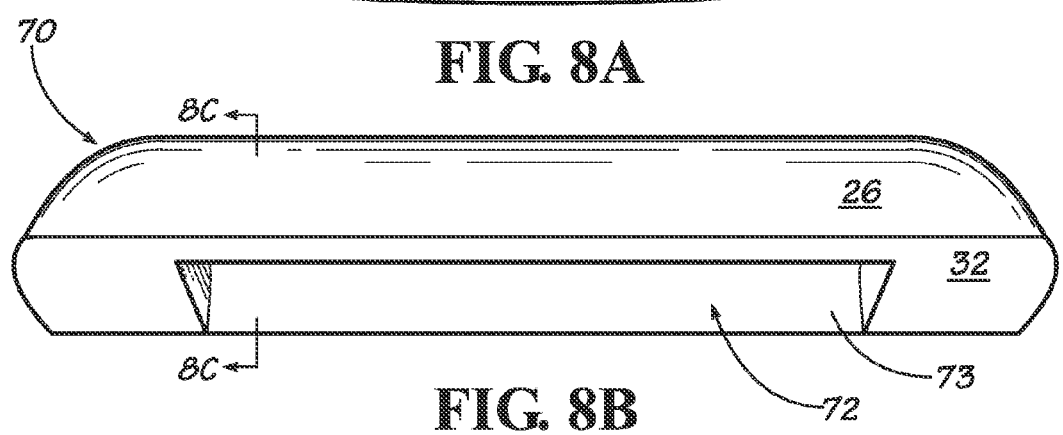
Figure 8C:
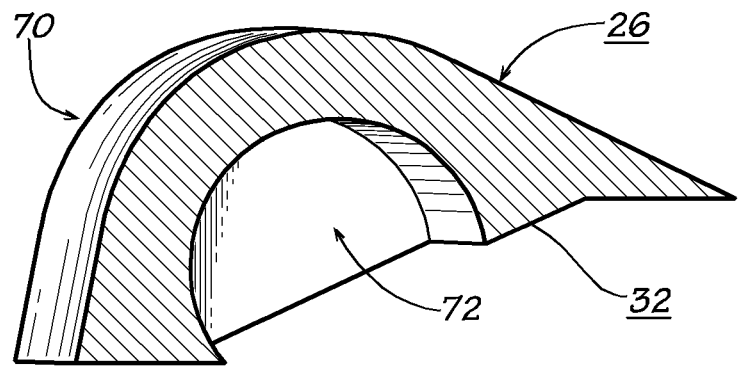

In one embodiment, an anchor 60 is first inserted into a hole 62, as shown in FIG. 7B, and the implant 50 is then mounted on the anchor 60 by inserting the anchor head 61 into opening 58 or opening 59 of the anchor slot 52 and moving the implant 50 so that the anchor 60 slides with the anchor slot 52 so that the anchor head 61 is captured within the anchor slot 52 and the implant 50 is properly positioned on the prepared bone surfaces 1010, 1011 (see FIG. 7C). If mounting holes 20 are provided, fasteners may be used to further secure the implant 50 to the bone.

In another embodiment, the implant 50 is positioned adjacent the anchor 60 and tapped or pushed such that the head 61 of the anchor 60 is forced past the neck 56 and into the anchor slot 52. If using this method of installation, it may be desired to provide a neck 56 that is made of a flexible material, such that the neck 56 flexes to accommodate the head 61 of the anchor 60.

In an alternative embodiment, an anchor 60 is first positioned within the anchor slot 52 on implant 50. Specifically, the head 61 of the anchor 60 is inserted into opening 58 or opening 59 of the anchor slot 52. Then the anchor 60 (with attached implant 50) is inserted into a hole 62. The anchor 60 may slide within the anchor slot 52 to the appropriate position to align with the pre-drilled hole 62 in the bone. If mounting holes 20 are provided, fasteners may be used to further secure the implant 50 to the bone.

The anchor slot 52 enables additional fixation between the rim portion 12 of the implant 50 and the bearing surface 1006, thus preventing loosening of the implant 50 caused by torsion forces. Anchor slot 52 is particularly desirable because it provides additional fixation while at the same time providing a smooth bearing surface 18 (which also minimizes torsion forces on the implant 50). Specifically, the anchor slot 52 does not extend through the rim portion 12, and thus, the heads 61 of the anchors 60 are not exposed on the bearing surface 18, but rather the bearing surface 18 is a continuous, smooth surface on which the femoral head can articulate.

The implant embodiments illustrated in FIGS. 3-6 are merely illustrative. More than a single anchor slot 52 may be provided on an implant 50. Moreover, an anchor slot 52 may have geometry different from what is shown so long as the anchor slot 52 is able to capture the head 61 of the anchor 60. It should also be understood that in other embodiments, the anchor slot 52 may be positioned on other portions of the implant 50 (e.g., the flange portion 14) and that any number of anchor slots 52 may be positioned on the rim portion 12, the flange portion 14, or both. Moreover, anchor slots may be provided on any type of acetabular implant and certainly their use is not limited to implants having the geometry shown in FIGS. 3-6.

The anchor 60 may be any type of fastener to secure the implant 50 to the bone. The embodiments shown in FIGS. 3-7C include an anchor 60 with an external thread. If desired, the outer thread may be made of a flexible material, such that the anchor 60 may be tapped or pushed into the hole 62. Other embodiments may include other bone-engaging structure (such as barbs), and in still other embodiments, the anchor 60 may not be provided with any bone-engaging structure at all (such as a smooth nail).

Any of the implants described herein may be made from a biocompatible material, such as wood, metal, polymer, composite, or ceramic. Some materials that may be used to make the implants include titanium, titanium alloys, steel, cobalt-chromium alloys, tantalum, magnesium, zirconium, zirconium alloys, bioglass, brushite, hydroxy-appetite, calcium sulfate, calcium phosphate, silicon oxide, and silk. The implants may be made from shape memory materials. Specific polymers that may be used include polyetheretherketone (PEEK), polymethyl methacrylate (PMMA), polyethyl methacrylate (PEMA), polyacrylate, poly-alpha-hydroxy acids, polycapropactones, polydioxanones, polyesters, polyglycolic acid, polyglycols, polylactides, polyorthoesters, polyphosphates, polyoxaesters, polyphosphoesters, polyphosphonates, polysaccharides, polytyrosine carbonates, polyurethanes, and copolymers or polymer blends thereof. Other polymeric materials may include polylactide and polyglycolide, including their copolymers, poly-(D,L-lactide-co-glycolide) and polyglycolide-co-trimethylenecarbonate; stereopolymers, such as poly-(L-lactide) or poly-Lactic acid (PLA), poly-(L-CO-D,L-lactide) and poly-(D,L-lactide), polyglactin acid (PGA), a combination thereof (PLA/PGA) or any derivative, combination, composite, or variation thereof, poly-(D,L-lactide-co-glycolide) (PDLLA-co-PGA), poly-(L-lactide) (PLLA), poly-(D-lactide) (PDLA), polyglycolide-co-trimethylenecarbonate, (PGA-co-TMC), poly-(L-CO-D,L-lactide), poly-(D,L-lactide), (PDLLA). The use of slow degrading and highly crystalline polymers, such as poly-(L-lactide) and poly(L-CO-D,L-lactide) stereocopolymers with a low D,L amount, amorphous polymers, such as poly-(L-CO-D,L-lactide) stereocopolymers with a high D,L amount of poly-(D,L-lactide), or fast-degrading copolymers, such as poly-(D,L-lactide-co-glycolide) or polyglycolide-co-trimethylenecarbonate, is envisioned and falls within the scope of this disclosure. The use of injectable or crosslinkable polymers, including, but not limited to, photopolymerizable and chemically polymerizable polymers and polymers that harden in situ, is also encompassed by this disclosure, including but not limited to the use of polymers of sebacic acid (SA), alone, or copolymers of SA and 1,3-bis (p-carboxyphenoxy) propane (CPP), or 1,6-bis (p-carboxyphenoxy) hexane (CPH), or poly(propylene fumarate) (PPF). Materials for implants are not limited to the foregoing and may also include any fully or partially degradable or erodible in a body chemical composition, including but not limited to carbohydrates and derivatives thereof, such as such as cellulose or hyaluronic acid. A modification of polymeric materials to adjust their structural, mechanical or chemical properties, or facilitate biological responses in tissues is envisioned and falls within the scope of this disclosure. Materials used to make implants may include a two phase polymer system wherein one phase degrades faster than another to allow for adequate strength and bone in-growth. The system may be a non-miscible blend. An example of the two phase polymer system is PDLA in combination with polyurethane. In addition, bioactive agents may be incorporated into the material comprising the implant to be released during the deformation or the degradation of the material. These agents are included to help promote bone regrowth. Examples include bone morphogenic proteins, antibiotics, anti-inflamatoies, angiogenic factors, osteogenic factors, monobutyrin, omental extracts, thrombin, modified proteins, platelet rich plasma/solution, platelet poor plasma/solution, bone marrow aspirate, and any cells sourced from flora or fawna, such as living cells, preserved cells, dormant cells, and dead cells. Other bioactive agents known to one of ordinary skill in the art may also be used. Furthermore, the polymeric materials can be formed as a composite or matrix and include reinforcing material or phases such as fibers, rods, platelets, and fillers. For example, the polymeric material can include glass fibers, carbon fibers, polymeric fibers, ceramic fibers, or ceramic particulates. Other reinforcing material or phases known to one of ordinary skill in the art could also be used.

FIGS. 8-11 illustrate another embodiment of an acetabular implant and a means by which to secure the acetabular implant onto the acetabular rim. Specifically, acetabular implant 70 may be provided with an undercut portion 72 that may be filled with epoxy 76 in order to adhere the acetabular implant 70 to the bone. FIGS. 8A-C illustrate structural features of some embodiments of acetabular implant 70, which include a bone-mating surface(s) 32, outer surface(s) 26, and at least one undercut portion 72 provided in the bone-mating surface 32 and having an opening 73 on the bone-mating surface 32.

In the illustrated embodiment, the outer surface 26 is shaped to replicate the acetabular rim and/or labrum but it should be understand that the shape of the acetabular implant 70 (as defined by the outer surface 26) is not limited to the illustrated embodiment but rather the acetabular implant attachment methodology discussed herein may be implemented on implants of any shape.

The bone-mating surface(s) 32 is preferably shaped to mate with the shape of the bone surface(s) upon which the acetabular implant 70 is seated. It may be any size or shape as needed to replace damaged and/or irregular bone. The undercut portion 72 may also be any desired size and/or shape as well and more than one undercut portion 72 may be provided. In use (see FIG. 9), the undercut portion 72 is filled with epoxy. When the acetabular implant 70 is seated on the bone, the epoxy 76 contacts the underlying bone surface and hardens or cures to securely attach the acetabular implant 70 to the bone.

Figure 10:
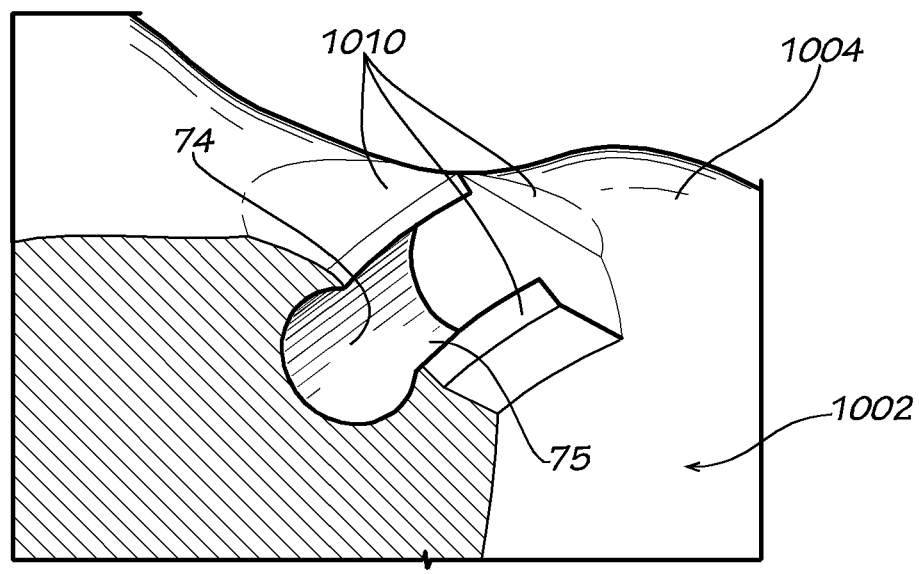
FIG. 10 is a partial cross-sectional view of a prepared bone surface on an acetabulum.

In other embodiments, the epoxy 76 may not be adhered to bone or only to bone. FIG. 10 illustrates a portion of the patient's pelvic bone 1000 that includes the acetabulum 1002 and acetabular rim 1004. The acetabular rim 1004 has been prepared to receive acetabular implant 70. However, in addition to prepared bone surfaces 1010 on which implant 70 will seat, a bone undercut 74 has also been provided in the bone and has an opening 75 on the bone.

Figure 11:
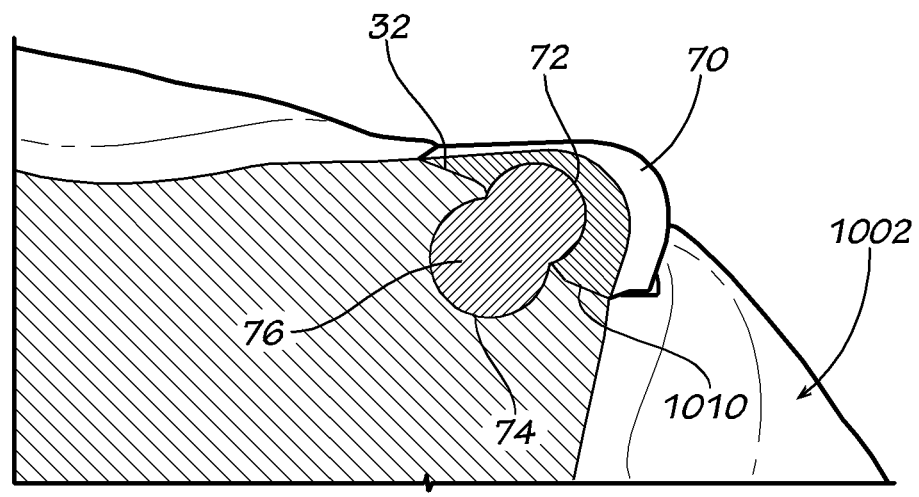
FIG. 11 is a partial cross-sectional view of the acetabular implant of FIGS. 8A-C positioned on the prepared bone surface of FIG. 10.

FIG. 11 illustrates the acetabular implant 70 attached to bone that includes a bone undercut 74, wherein the bone-mating surfaces 32 of the implant contact the prepared bone surfaces 1010, and the undercut 72 of the acetabular implant 70 generally aligns with the undercut 74 of the bone. It is not necessary for the two undercuts 72, 74 to align exactly, nor is it necessary for the bone preparation surfaces 1010 to exactly match the shape of the bone mating surfaces 32. Rather, only an approximate alignment and/or matching is required because epoxy 76 fills the undercuts 72, 74 and can thus fill any space or cracks that are created between the bone and the acetabular implant 70 (including any cracks between the bone-mating surfaces 32 and prepared bone surfaces 1010). The use of undercuts 72, 74 and epoxy 76 allows for less precision in cuts that are made to the bone, saving time and reducing complexity during surgery. When the epoxy 76 hardens (or is cured), it securely attaches the acetabular implant 70 to the bone.

Figure 9:
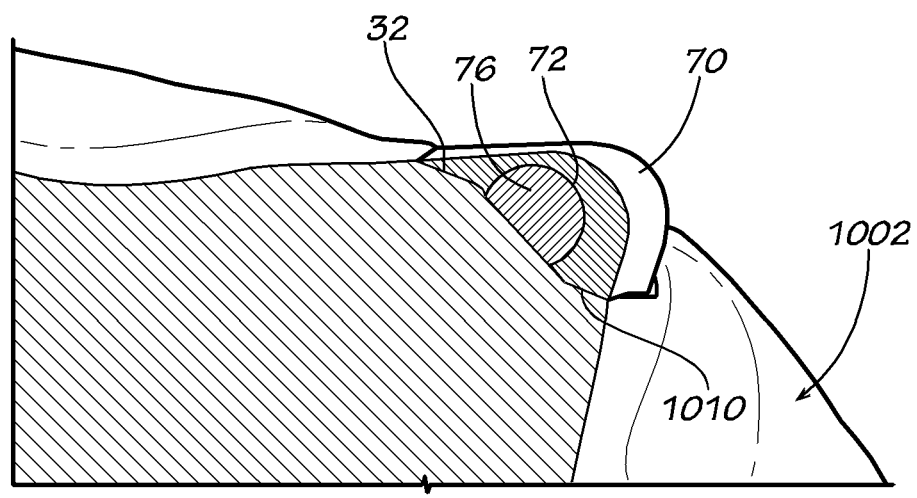
FIG. 9 is a partial cross-sectional view of the acetabular implant of FIGS. 8A-C positioned on a prepared bone surface of an acetabulum.

In certain embodiments, the adhesive and/or bonding properties of the epoxy 76 may be responsible for only part of the secure attachment. The shape of the undercut(s) 72 and/or 74 may also contribute to the security of the attachment of the acetabular implant 70 on the bone. Specifically, as shown in FIGS. 9 and 11, the cross-sectional shape of undercut 72 narrows at opening 73. Similarly the cross-sectional shape of undercut 74 narrows at opening 75. In this way, the two undercuts 72, 74 form a "figure-8". The narrowed openings 73, 75 prevent pull-out of the epoxy from either undercut 72, 74 and thus enhances retention of the acetabular implant 70 on the bone. Thus, strong fixation between the acetabular implant 70 and the bone is achieved (due to the adhesion of the epoxy and, in some embodiments, the shape of the undercuts 72, 74), while at the same time allowing for less precision in cuts made to the bone.

The epoxy 76 may be filled in a variety of ways. For example, epoxy 76 may be inserted into the undercut(s) 72 and/or 74 prior to attachment of the acetabular implant 70 to the bone. Alternatively, the acetabular implant 70 may be provided with apertures (not shown) through which to inject epoxy 76. Examples of epoxy 76 include, but are not limited to, epoxy, bone cement, or biocompatible polymer, gel, epoxy, or cement. Further non-limiting examples of potential materials that may be used for epoxy 76 are described in the following references: U.S. Patent Application Publication No. 2006/0051394 titled "Biodegradable Polyurethane and Polyurethane Ureas," U.S. Patent Application Publication No. 2005/0197422 titled "Biocompatible Polymer Compositions for Dual or Multi Staged Curing," U.S. Patent Application Publication No. 2005/0238683 titled "Biodegradable Polyurethane/Urea Compositions," U.S. Patent Application Publication No. 2007225387 titled "Polymer Compositions for Dual or Multi Staged Curing," U.S. Patent Application Publication No. 2009324675 titled "Biocompatible Polymer Compositions," U.S. Patent Application Publication No. 2009175921 titled "Chain Extenders," and U.S. Patent Application Publication No. 2009/099600 WO 2009/043099 titled "High Modulus Polyurethane and Polyurethane/Urea Compositions." Each of the prior references is herein incorporated by reference. In some embodiments, the epoxy is expandable or form shaping when hit with energy (thermal energy, electrical energy, etc.).

Acetabular implant 70 is shown merely for illustrative purposes. The shape of acetabular implant 70 may vary. Moreover, the number, shape, and positioning of undercuts 72, 74 may vary as well.

Figure 12:
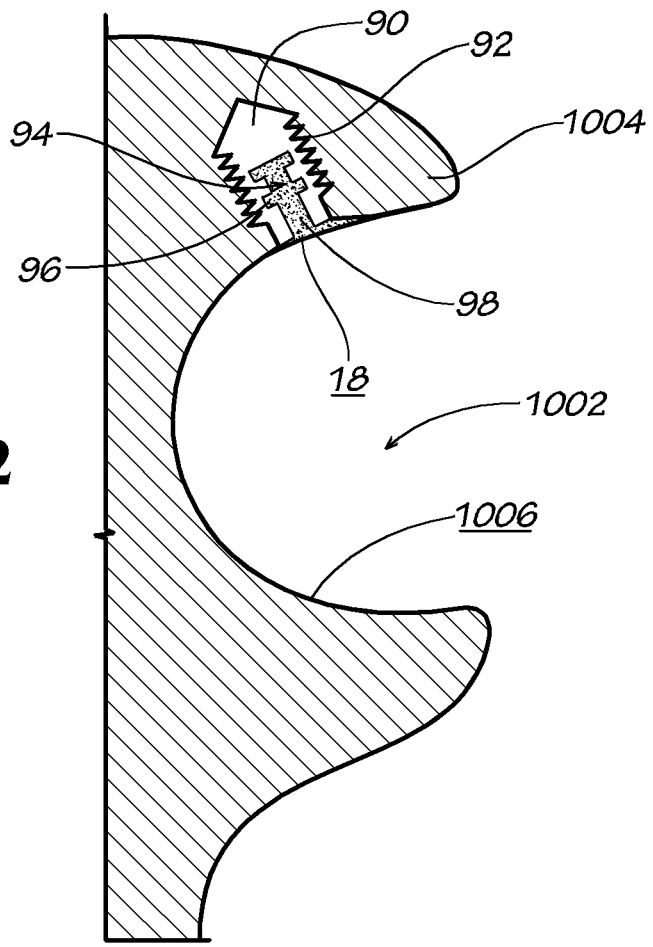
FIG. 12 is a cross-sectional view of an embodiment of a plug filled with injectable material, shown inserted into an acetabulum.
Figure 13:
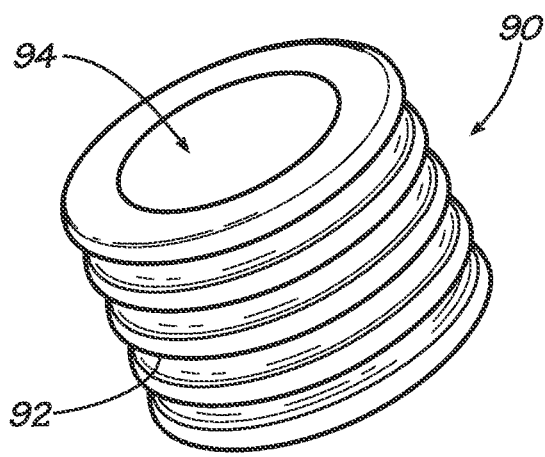
FIG. 13 is a perspective view of another embodiment of a plug.
Figure 14A:
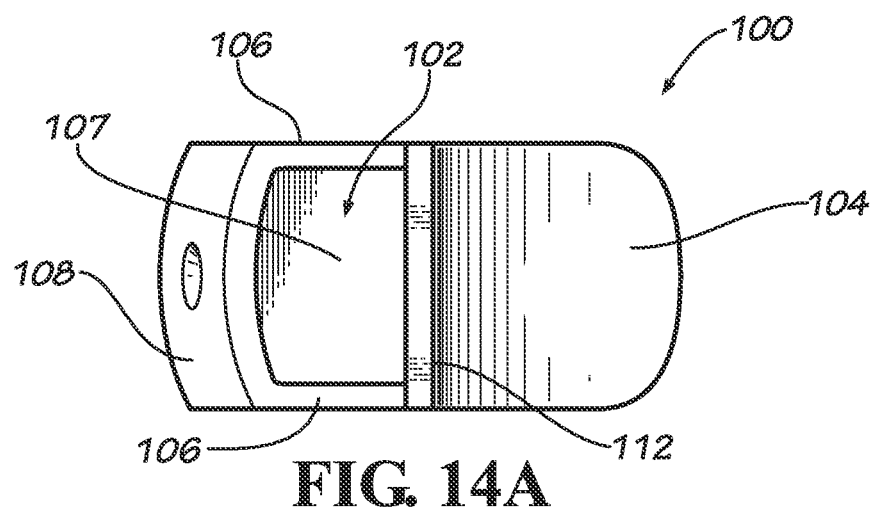
FIGS. 14A-E are various views of one embodiment of a mold for use in repairing acetabular defects.
Figure 14B:
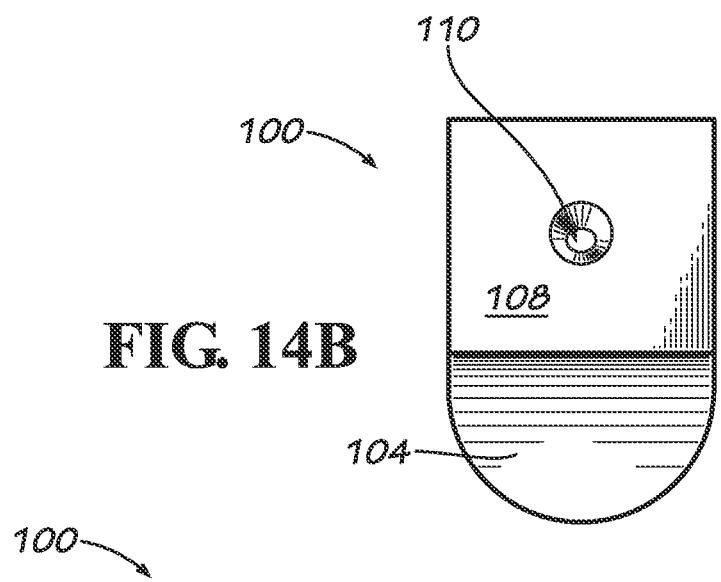
Figure 14C:
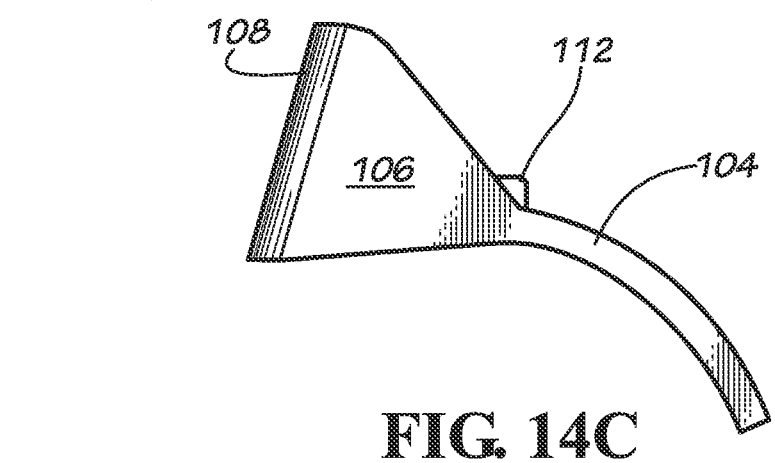
Figure 14D:
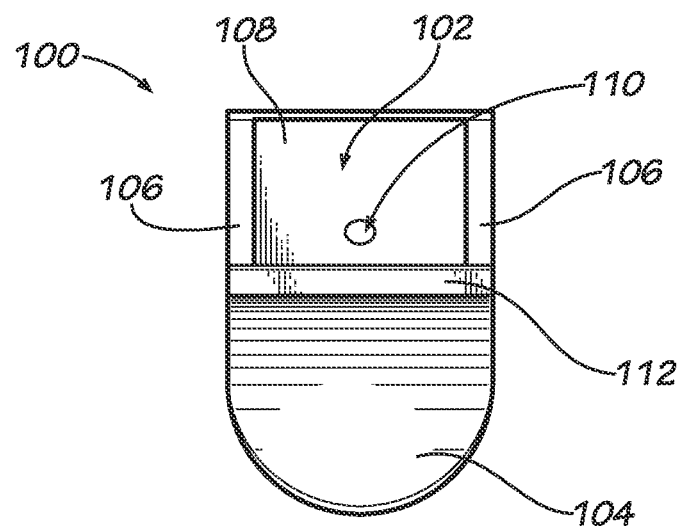
Figure 14E:
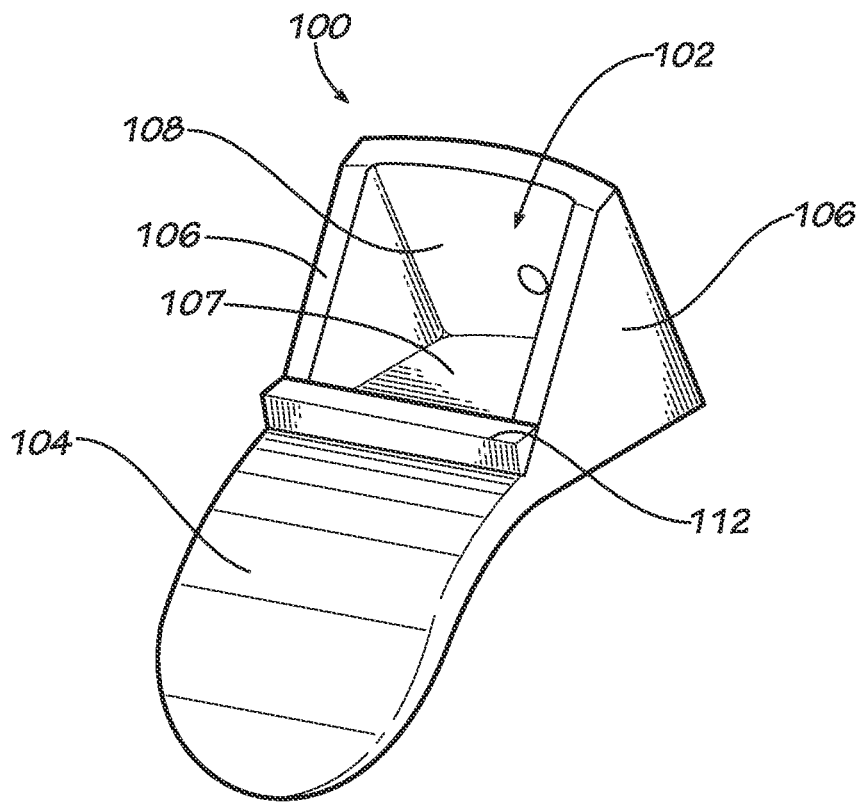

Implants for treating FAI may also include the use of injectable materials that cure and harden to fill any depressions and/or lesions within the acetabulum. For example, FIG. 12 shows a plug 90 that is inserted into a portion of the patient's acetabulum 1002. If desired, the plug 90 may be provided with outer threads 92 to help secure the plug 90 within the bone. The plug 90 in FIG. 12 is slightly tapered along its length, whereas the plug 90 in FIG. 13 is not tapered but rather cylindrical. The plug 90 may be inserted by any means known to one of skill in the art. For example, the outer threads 92 may be self-tapping to secure the plug 90 directly into the bone. Alternatively, the surgeon may pre-drill a hole into the bone, and then insert or tap the plug 90 into the pre-drilled hole. The plug 90 defines a cavity 94 that may optionally include recessed portions 96. For example, the plug 90 shown in FIG. 12 has recessed portions 96, whereas plug 90 in FIG. 13 does not. The cavity 94 may have any shape, including, but not limited to, tapered, conical, or non-tapered.

The plug 90 is inserted into the acetabulum 1002 so that the opening to the cavity 94 is exposed within the acetabulum 1002. Injectable material 98 may be injected into the cavity 94 of the plug 90 (including any recessed portions 96 that may be provided within the cavity 94). If provided, the recessed portions 96 provide a greater surface area for the injectable material 98 to grip onto, thus preventing the material 98 from separating from the plug 90. In some embodiments, apertures, slits, slots, etc. (not shown) may be provided through the plug wall so that some of the injectable material 98 contacts the surrounding bone to further stabilize the plug 90 within the bone. Examples of injectable material 98 include, but are not limited to, biocompatible polymer, gel, epoxy, cement, and any of the materials identified above in the discussion of the embodiment of FIGS. 8-11.

If desired, the injectable material 98 may be filled in excess of the volume of the cavity 94, such that some of the injectable material 98 over flows the plug 90, rising adjacent to or covering a portion of the bearing surface 1006 of the acetabulum 1002. Then the injectable material 98 may be allowed to harden or cure. Upon hardening, the injectable material 98 simulates the bone to thereby fill in the depression and/or lesion. Surface 18 of the injectable material 98 may act as a bearing surface for the femoral head. If desired, surface 18 may be shaped, cut, or otherwise refined or contoured to simulate the bearing surface 1006 of the acetabulum 1002.

In other embodiments (not shown), the plug 90 is not provided with a cavity 94. Rather, the plug 90 may be inserted into the bone as described above, and the plug 90 itself (rather than the injectable material 98) simulates bone, and acts to repair lesions in the bone.

FIGS. 14 and 15 illustrate other ways to use injectable material 98 to repair irregular and/or damaged bone in the acetabulum 1002. Specifically, certain embodiments provide a mold 100 with a cavity 102 to receive injectable material 98. When the injectable material 98 hardens, it replicates acetabular anatomy, such as, but not limited to, the labrum and/or acetabular rim 1004.

FIGS. 14A-E illustrate structural features of one embodiment of mold 100, which can include a cavity 102 that is defined by sidewalls 106, an end wall 108 (which contains at least one aperture 110), and a bottom wall 107. The cavity 102 provided on the mold 100 may be of any suitable shape or size and, if desired, may be shaped to recreate the desired features of the acetabulum 1002 and/or rim 1004.

The mold 100 may also include, but does not have to include, a tongue 104 extending from the bottom wall 107 that can act to distract the femoral head 1014 and a dam 112 to provide protection against leakage of the injectable material 98. The dam 112 may be integrally formed with the mold 100, or it may be a separate component that is attached to the mold 100. If the dam 112 is separately attached to the mold 100, then the mold 100 may have a groove (for example, where the tongue 104 meets bottom wall 107 at the cavity 102) to receive the dam 112. If desired, the dam 112 may be made of a pliable material that performs as a gasket in preventing leakage of the injectable material 98. It should be understood that a dam 112 may be positioned anywhere along the length of the tongue 104 (for example, mid-way down the tongue 104), or on other locations on the mold 100. For example, a dam 112 may be provided along the tops of the sidewalls 106 and/or end wall 108 (thus contacting the bone when the mold 100 is in use) or along the inner corners of the cavity 102. The need for a dam 112, the positioning of a dam 112, and/or the materials from which a dam 112 is made may depend on the viscosity and other properties of a particular injectable material 98.

Figure 15A:
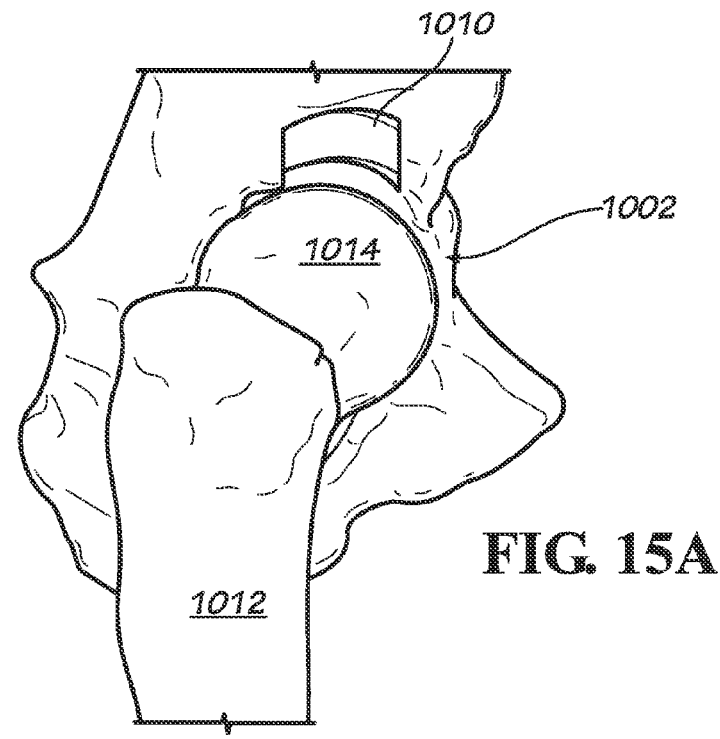
FIG. 15A-C illustrate methods of using the mold as shown in FIGS. 14A-E.
Figure 15B:
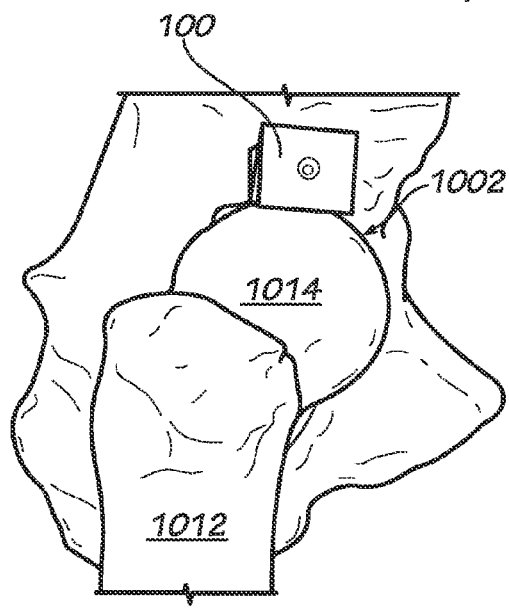
Figure 15C:
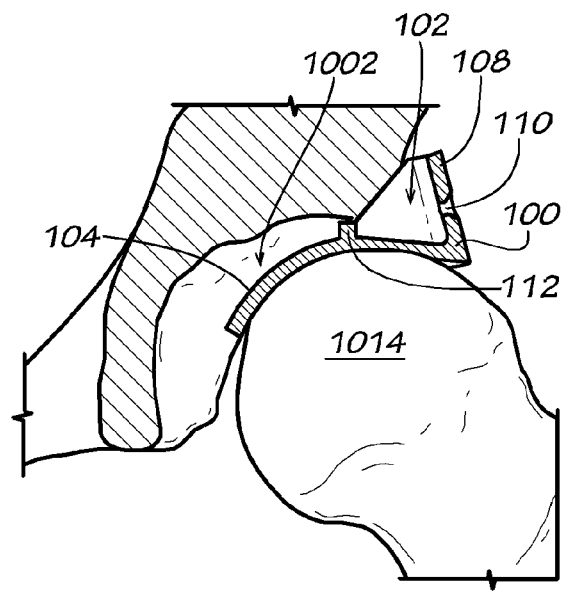

Methods of using the mold 100 are illustrated in FIGS. 15A-C. As shown in FIG. 15A, a prepared bone surface 1010 may be cut into bone to remove any irregular and/or damaged bone. It should be understood that this step may not be required in all patients. If desired, holes may be drilled into the prepared bone surface 1010 to assist with adhesion as described below. Next, the tongue 104 of the mold 100 may be inserted between the femoral head 1014 and the acetabulum 1002, as shown in FIGS. 15B and 15C. In some embodiments, the mold 100 may include more than one tongue 104. The tongue 104 may be used as a lever to distract the femoral head 1014 from the acetabulum 1002 and provide the desired amount of working space for the surgeon. Note that tongue 104 may not be used in all cases.

When the mold 100 is inserted as in FIG. 15C, the end wall 108 and aperture 110 are exposed, such that injectable material 98 may be injected into the aperture 110, filling the cavity 102 and contacting (and adhering to) the prepared bone surface 1010. If holes are drilled into the prepared bone surface 1010, then the injectable material 98 may fill such holes to enhance adhesion and retention of the injectable material 98 on the acetabulum 1002. The dam 112 prevents injectable material 98 from filling the joint space between the femoral head 1014 and the acetabulum 1002 (or otherwise escaping the cavity 102 into undesirable regions). When the injectable material 98 hardens, it forms a structure that replicates anatomy of the acetabulum 1002 and/or rim 1004.

There are various ways to remove the mold 100 from the acetabulum 1002 area while leaving the hardened injectable material 98 in place. For example, the injectable material 98 may shrink and pull away from the sides of the cavity 102 as the material 98 hardens. The sidewalls 106 and end wall 108 may be draft-angle walls to provide for easier removal of the mold 100. As a further example, air and/or saline (or other fluids) may be injected into aperture 110 when the injectable material 98 hardens, thus forcing the hardened material 98 away from the mold 100. Still other methods of removing the mold 100 would be known to one of skill in the art.

Embodiments of acetabular implants described herein may be more effective than simply using osteotomy to remove or reshape bone. For example, implants provide a bearing surface 18 that may fill in depressions and/or lesions in the bone that might not otherwise be treatable with only osteotomy. Implants might also help alleviate the risk that the bone will grow back, minimizing the likelihood that additional surgeries will be needed to correct problems caused by bone regrowth.

Certain embodiments of the implants and/or injectable materials described herein may be used to replace the labrum and/or acetabular rim 1004 and thereby help capture the head of the femur. Optionally, portions of such implants (e.g., the rim portion 16 and/or the ridge 15) may be formed of a more flexible material than the remainder of the implant to replicate the texture of the labrum. Thus, embodiments of the acetabular implants described herein help replace whatever portion of the patient's natural labrum that was removed during surgery. This is in comparison to known techniques that did not provide any structure to replace the patient's labrum. The use of acetabular implants may help reduce the likelihood that additional surgeries will be needed to correct problems caused by loss of the labrum.

Figure 16:
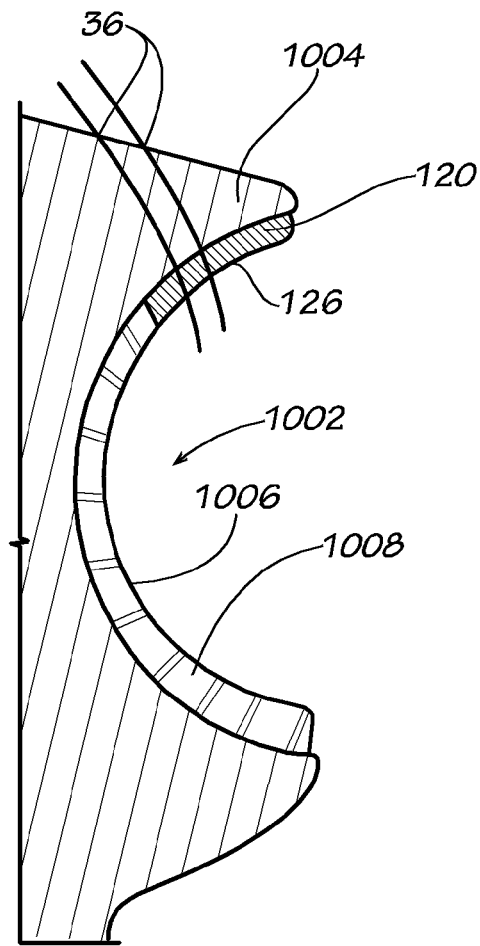
FIG. 16 is a cross-sectional view of one embodiment of a biomedical textile positioned within an acetabulum.

In addition to replacing the labrum, it may be desirable to provide an implant to replace cartilage 1008 within the acetabulum 1002. Thus, as shown in FIG. 16, rather than leaving exposed bone, a biomedical textile 120 may be secured within the acetabulum 1002 to replace any damaged or non-viable cartilage 1008. It may be desirable for at least a portion of the exposed surface 126 of the biomedical textile 120 to substantially align with the bearing surface of the acetabulum and thereby create a continuous bearing surface for the femoral head.

The biomedical textile 120 may include any textile made from interlaced fibers. The fibers may be natural, artificial, or a blend thereof, such as but not limited to metallic fibers, polymeric fibers (such as polytetrafluoroethylene), biodegradable polymers (such as polylactic and polyglycolic acids), polyamides, polyurethanes, silk, collagen, or chitosan. Specific examples of commercially available biomedical textiles 120 include Gore-Tex® (manufactured by W.L. Gore & Associates, Inc.), or Dacron® (manufactured by Invista, Inc.). The biomedical textile 120 may be impregnated with antibiotics or osteo-conductive materials to stimulate bone re-growth.

Figure 17:
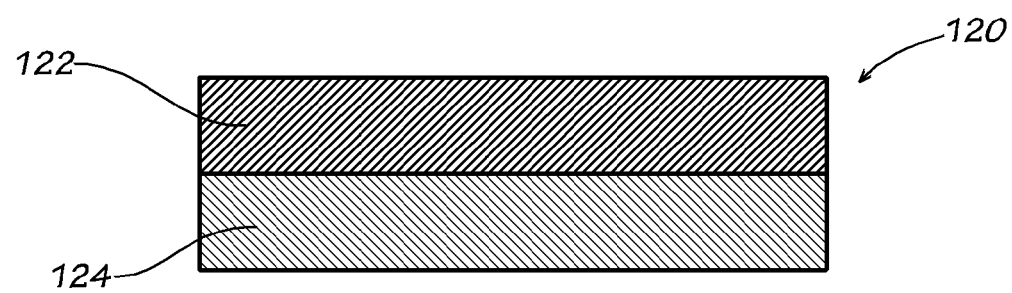
FIG. 17 illustrates another embodiment of a biomedical textile.

As shown in FIG. 17, the biomedical textile 120 may comprise one or more layers 122, 124, each having different properties. First layer 122 may be positioned adjacent to the patient's bone and may be provided with a rougher texture that might help stimulate growth of bone and/or cartilage. In certain embodiments, first layer 122 may also include antibiotics or osteo-conductive materials to stimulate bone re-growth. Second layer 124 may be exposed to the acetabulum 1002, and thereby come into contact with the femoral head. Thus, second layer 124 may have a smoother texture to provide a smooth bearing surface for the femoral head. Any type and/or placement of layers is within the scope of the invention. The biomedical textile 120 may be secured to the bone with fixation elements, such as wires or sutures 36 as shown in FIG. 16. Other methods of attachment may include adhesive, bone screws, anchors, etc.

The biomedical textile 120 shown in FIG. 16 is secured to the acetabulum 1002 proximate the acetabular rim 1004. But the textile 120 may be secured anywhere within the acetabulum 1002 where it is necessary to replace cartilage 1008.

Additionally, the biomedical textile 120 may be wrapped around or integrated with acetabular implants as described herein. For example, the biomedical textile 120 may be interposed between an acetabular implant and the underlying bone. A portion of the biomedical textile 120 may protrude out from underneath the acetabular implant, such that a border of the biomedical textile 120 is exposed. Such an exposed border may help reduce force and/or irritating contact between the patient's bone and the implant.

Biomedical textiles 120 offer several benefits. For example, such materials may be cut into any shape and/or size that is needed to replace the cartilage 1008. Biomedical textiles 120 are biocompatible and reduce the likelihood of irritation to the patient. Such materials are complaint (like cartilage is compliant) and yet also tough to withstand the shear forces imposed by the femoral head. Finally, biomedical textiles 120 may be implanted using minimally invasive techniques (such as endoscopically or through a small incision).

FIGS. 18-31 illustrate embodiments of devices and methods that may be used to prepare the bone for an acetabular implant. FIGS. 18-21 illustrate embodiments of a guide jig 130 comprising a cradle 132 and a plurality of blocks 134 movably coupled to the cradle 132. The cradle 132 and the blocks 134 define a central aperture 138 that can be used as a template for a cutting tool to prepare bone surfaces to receive acetabular implants.

Figure 18A:
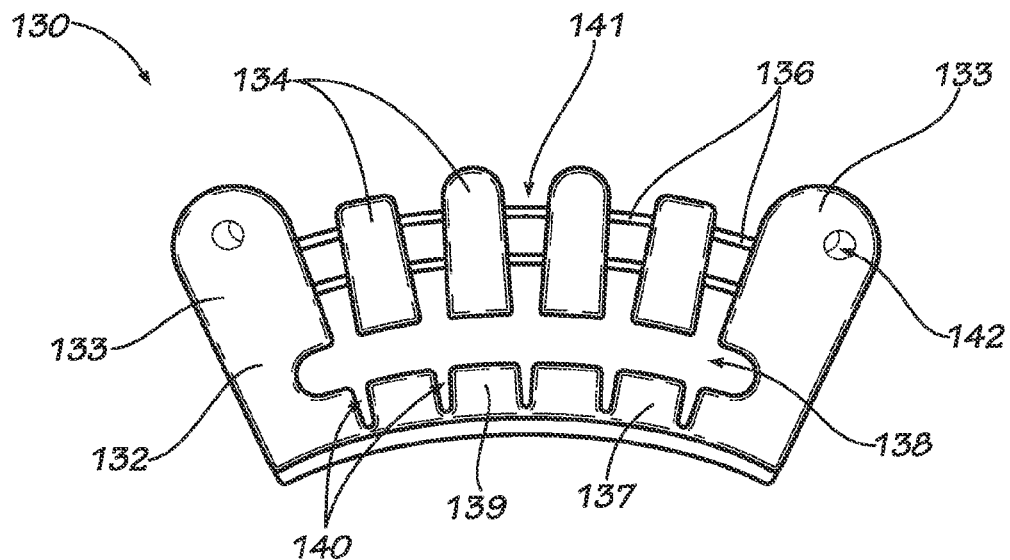
FIGS. 18A-B are views of one embodiment of a guide jig.
Figure 18B:
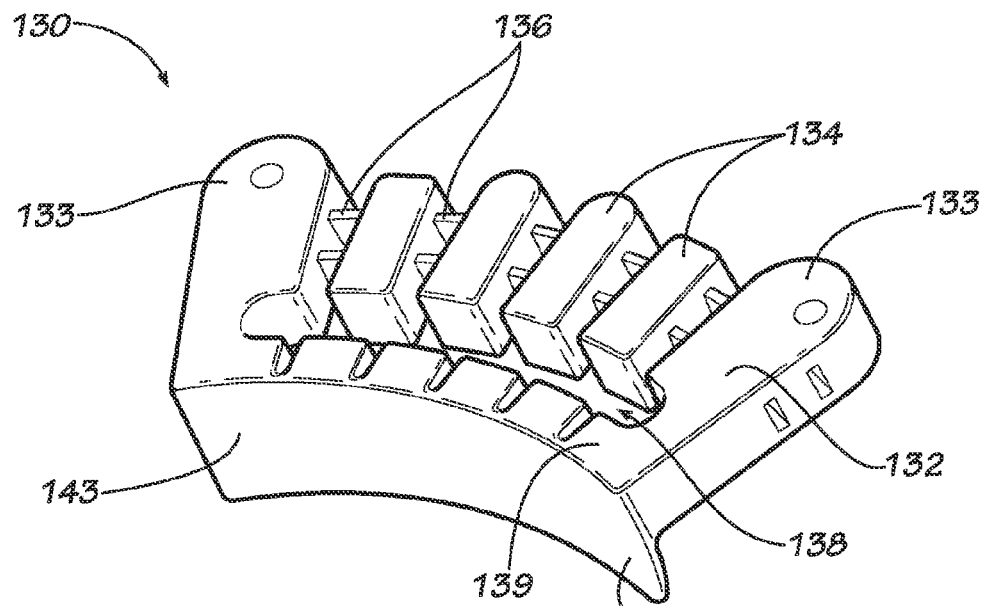
Figure 19:
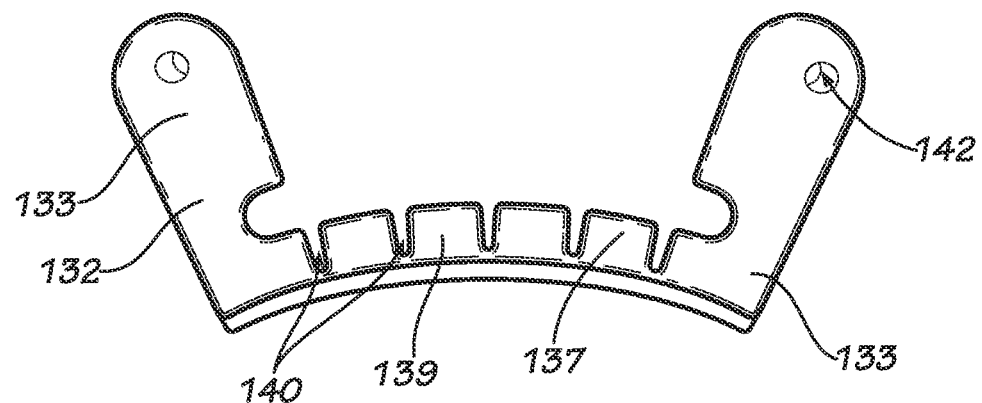
FIG. 19 is a top perspective view of the cradle of the guide jig of FIGS. 18A-B in isolation.

Embodiments of the guide jig 130 may include a cradle 132 that includes side arms 133 and lower arm 139. As shown in FIGS. 18A and 19, the side arms 133 are angled with respect to one another. In other embodiments, however, the side arms 133 may be parallel. The side arms 133 are connected with a lower arm 139 that spans between the side arms 133. The lower arm 139 may be curved or straight. Lower slots 140 may be provided in lower arm 139 to form teeth 137. Such slots 140 can permit the lower arm 139 to flex and thereby impart flexibility to the adjustably guide jig 130, as discussed below. In other embodiments, the lower arm 139 is rigid. In some embodiments, the lower arm 139 includes a ledge 143 that extends downwardly relative to the side arms 133 and may include a curved inner surface 145. As described below, such a ledge 143 may assist when positioning and stabilizing the guide jig 130 on the bone.

In certain embodiments, at least one web 136 spans the side arms 133 of the cradle 132. The web 136 may comprise wire, strips or strings of material, coils, or springs made from a variety of materials, such as but not limited to any type of biocompatible metal or polymer. Specific examples include, but are not limited to, instrument grade metals, memory metals, stainless steel, Nitinol® (manufactured by Nitinol Devices and Components of Fremont, Calif.), or any polymers identified in this disclosure. Still other materials are known to one of skill in the art. In the embodiments shown in the figures, the web 136 comprises two strips of material. In other embodiments, the web 136 may comprise fewer or more strips of material.

Figure 20:
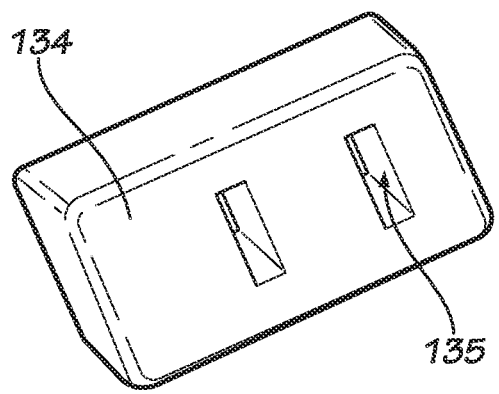
FIG. 20 is a top perspective view of a block of the guide jig of FIGS. 18A-B in isolation.

Certain embodiments of the guide jig 130 also comprise a plurality of blocks 134 that are coupled to the web 136. Specifically, the blocks 134 are strung onto the web 136 through slots 135 defined in the blocks 134 (as shown in FIG. 20). Upper slots 141 may be formed between adjacent blocks 134. The number, shape, and dimension(s) of the blocks 134 may differ from those illustrated and are contemplated herein. The blocks 134 need not have the same geometry.

The constituent parts of the guide jib 130 may be made from any material, including, but not limited to, any material identified in this disclosure.

Figure 2A:
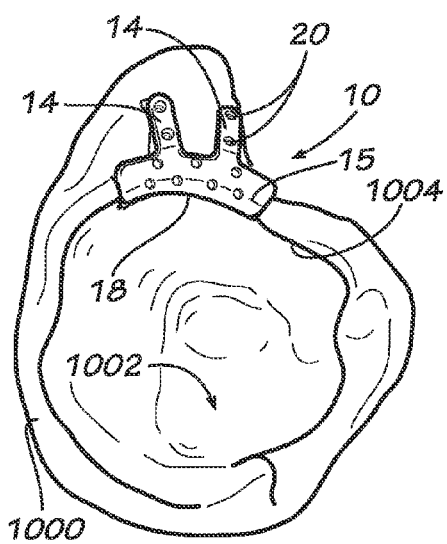
FIGS. 2A-F illustrate other embodiments of acetabular implants, shown attached to the bone, or exploded from the bone.
Figure 2B:
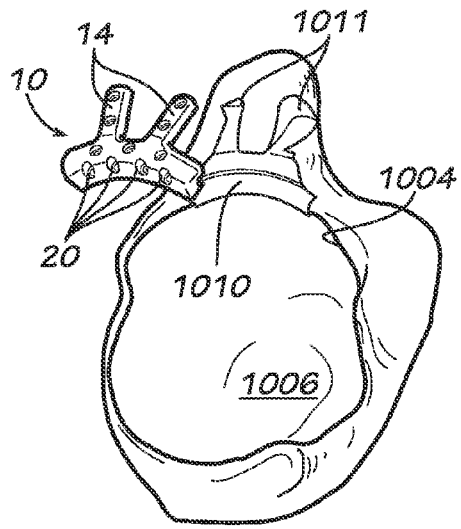
Figure 2C:
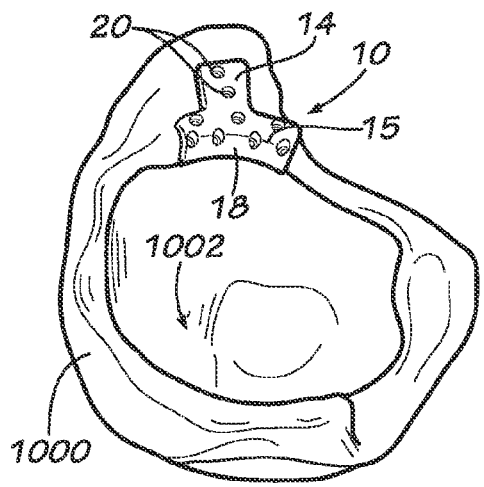

Together, the cradle 132 and the blocks 134 define a central aperture 138 that provides a template for cutting bone. The shape of the central aperture 138 (and thus, the shape of the prepared bone surfaces) may be adjustable. For example, in certain embodiments the blocks 134 can slide back and forth on the web 136, thus altering the number and shape of the upper slots 141. If the blocks 134 are pushed to the left side arm 133, for example, then there may be provided a large upper slot 141 near the right side arm 133, which may provide a template for bone preparation surface 1011 (for a flange portion 14 of an implant 10) as shown in FIG. 2B. As another example, the web 136 may be flexible such that the blocks 134 may be pushed closer to the lower arm 139 of the cradle 132, or may be pulled away from the lower arm 139, to vary the shape and/or size of the central aperture 138. Thus, flexing or moving the web 136 may create a wider or thinner central aperture 138. Moreover, the web 136 may have elastic properties that permit the side arms 133 to be pushed closer to each other or stretched further from each other. In certain embodiments, the lower arm 139 may flex to alter the radius of curvature of the central aperture 138. In some embodiments, the lower arm 139 is formed of teeth 137 are not connected together but rather are mounted on a web (similar to web 136) that extends between the side arms 133. The teeth 137 may slide on the web to impart additional flexibility to the guide jug 130.

In some embodiments, the guide jig 130 is adapted to conform to the patient's anatomy and be adjusted to create a customized cutting template that addresses the malformations and/or maladies of a particular patient's acetabular anatomy. In this way, the guide jig 130 affords more intraoperative flexibility for preparing acetabular bone surfaces than more standardized instrumentation. In some embodiments, parts of the guide jig 130 are made from pliable materials to permit bending, stretching or otherwise relative movement between the guide jig 130 parts. Such movement may help to allow the guide jig 130 to mold around or otherwise conform to the anatomy of a patient. In other embodiments, the guide jig 130 is substantially rigid. In still other embodiments, parts of the guide jig 130 are pliable while others are rigid. Certain embodiments of the guide jig 130 may provide for attachment of a pliable material on the posterior surface of the guide jig 130 to facilitate conformance of the guide jig 130 to the bone. In still other embodiments, the guide jig 130 may permit removal of material from the posterior surface of the guide jig 130 to facilitate conformance of the guide jig 130 to the bone.

Figure 21:
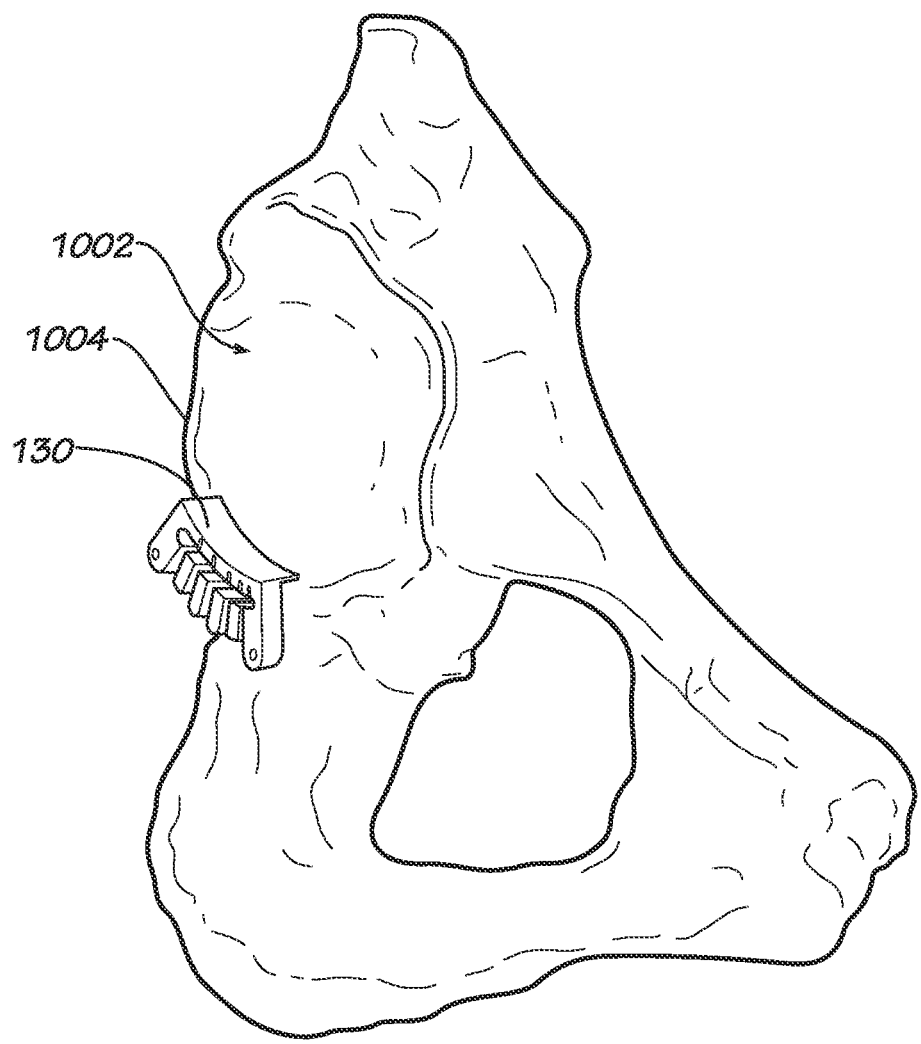
FIG. 21 shows the guide jig of FIGS. 18A-B positioned on an acetabular rim.

In use, the guide jig 130 is positioned over the acetabular rim 1004 so that the ledge 143 extends into the acetabulum 1002 and the side arms 133 extend outwardly from the rim 1004, as shown in FIG. 21. The central aperture 138 may be aligned over the portion of irregular and/or damaged bone that is meant to be removed. The guide jig 130 may be adjusted or flexed to obtain the desired shape and size of the central aperture 138. If desired, fixation holes 142 may be provided in any portion of the guide jig 130 (e.g., cradle 132, blocks 134, etc.) to receive anchors to attach the guide jig 130 to the bone and retain the shape of the desired central aperture 138. The inner surface 145 of ledge 143 may serve to distract the femoral head from the acetabulum and/or protect the femoral head during cutting. Then a cutting tool may be inserted into the central aperture 138 to cut the bone to prepare the bone surface for receipt of an implant. The cutting tool may be any type of tool known to one of skill in the art, such as a knife, a cutter, or a burr. If desired, the cutting tool may be provided with a guide bushing.

Certain embodiments of other devices for use in preparing bone surfaces for implants are shown in FIGS. 22-31. Specifically, certain embodiments provide a guide jig 150 that may receive a plurality of modular cutting inserts, such as cutting inserts 166, 176, 202. The cutting inserts 166, 176, 202 may be provided with cutting apertures 170, 174, 178, 204 of various shapes and sizes through which the surgeon may insert a cutting tool to prepare bone surfaces.

FIGS. 22A-E illustrate the structural features of one embodiment of the guide jig 150, which includes a ledge 160, a cup 156 that extends downwardly from the ledge 160, and an insert aperture 162 provided in the ledge 160. The cup 156 includes an outer surface 157 and inner surface 159. The inner surface 159 may be curved to define a hollow 158.

Figure 26:
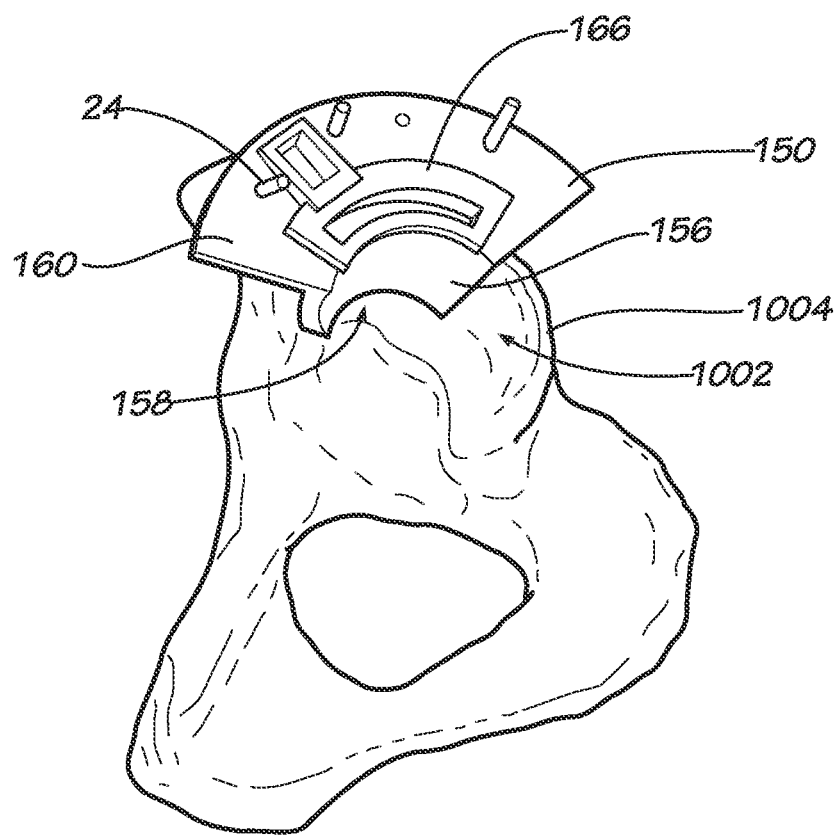
FIG. 26 is a top perspective view of the guide jig with cutting insert of FIG. 25 positioned on an acetabular rim.

In use, the cup 156 of the guide jig 150 is inserted against the acetabulum 1002 and the ledge 160 extends over the acetabular rim 1004, as shown in FIG. 26. The hollow 158 may receive the patient's femoral head 1014 (and may distract the femoral head 1014 from the acetabulum 1002). The curvature of the outer surface 157 and inner surface 159 of the cup 156 may vary depending upon the patient's anatomy.

Figure 22A:
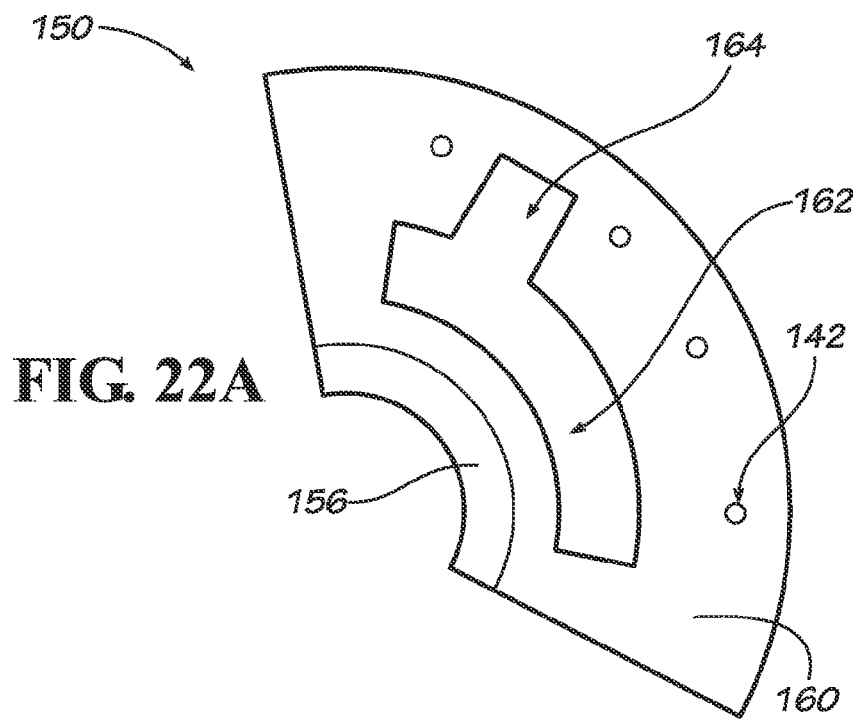
FIGS. 22A-E are various views of another embodiment of a guide jig.
Figure 22B:
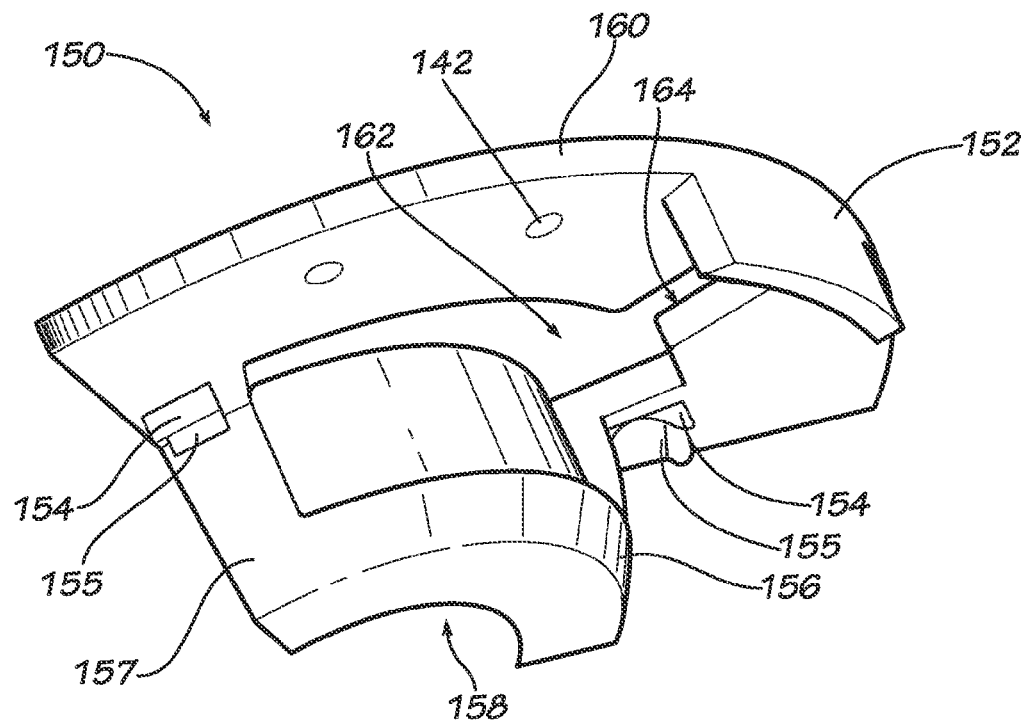
Figure 22C:
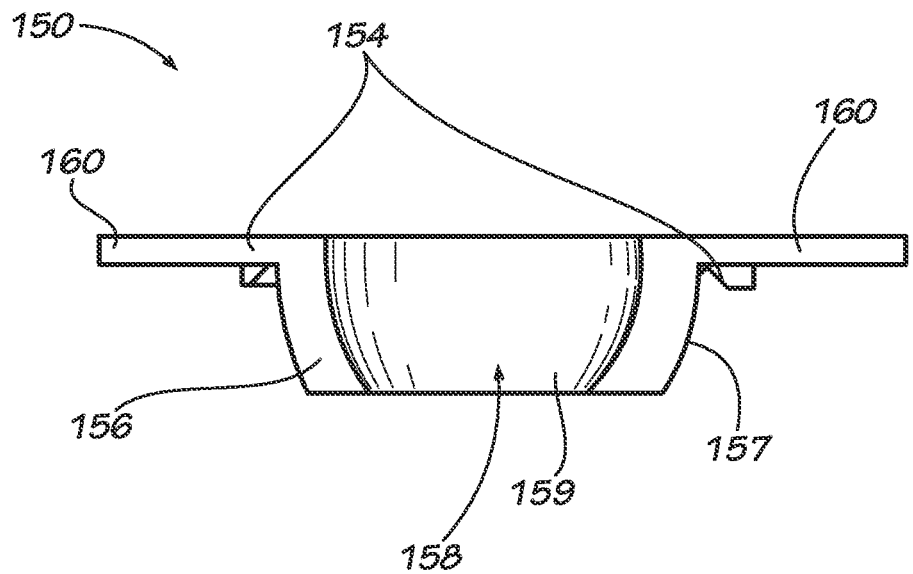
Figure 22D:
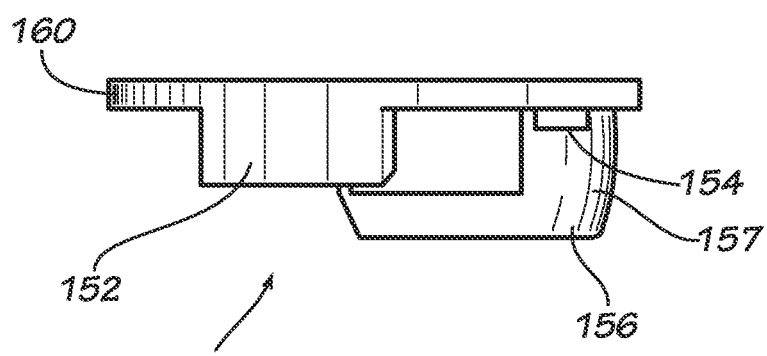
Figure 22E:
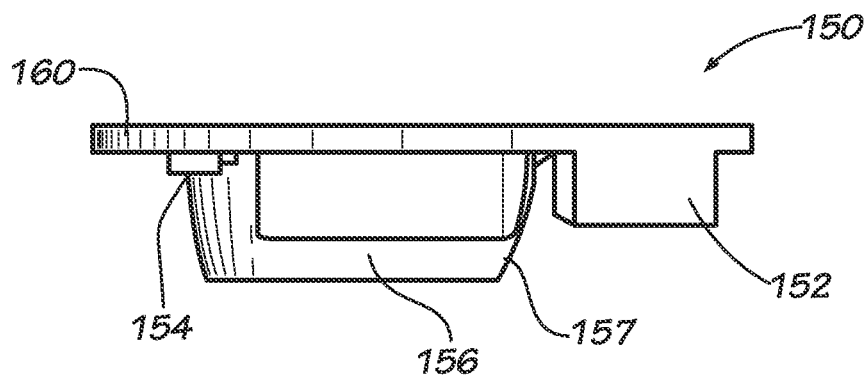
Figure 25:
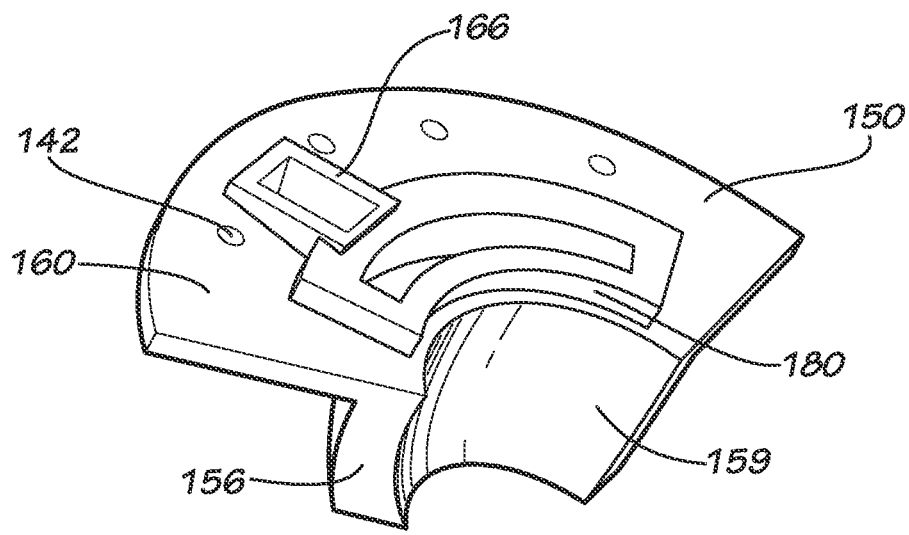
FIG. 25 is a top perspective view of the cutting insert of FIGS. 23A-B positioned in the guide jig of FIGS. 22A-E.

Certain embodiments of the guide jig 150 may be provided with structure to stabilize the jig 150 on the bone. For example, as best seen in FIG. 22B, a lip 154 may extend downwardly from ledge 160 to create a stabilizing surface 155 for resting upon the patient's acetabular rim 1004. Any number of lips 154 and resulting stabilizing surfaces 155 may be provided on the guide jig 150 so as to contact multiple points of the acetabular rim 1004. Additionally, a tab (or tabs) 152 may be provided on the underside of the ledge 160 to rest upon the patient's bone to provide stability near the outer perimeter of the ledge 160. The location and geometry of the lip(s) 154 and/or the tab(s) 152 may vary depending upon the patient's anatomy and could be based on pre-operative diagnostic imaging such as MRI or CT scans. Certain embodiments may include a plurality of fixation holes 142 that receive bone anchors 24 to secure the guide jig 150 to the bone.

In certain embodiments, the guide jig 150 is provided with at least one insert aperture 162 in ledge 160 to receive a cutting insert, such as cutting inserts 166, 176 (see FIGS. 23 and 24). The insert aperture 162 can be of any shape and size suitable to accommodate the size and shape of the cutting inserts. Furthermore, in some embodiments multiple insert apertures 162 may be provided on a jig 150.

Figure 2D:
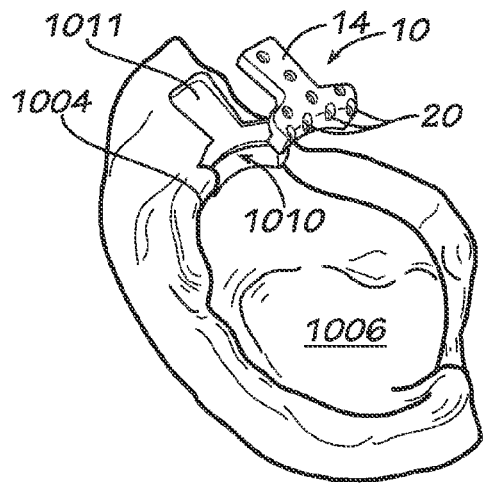
Figure 2E:
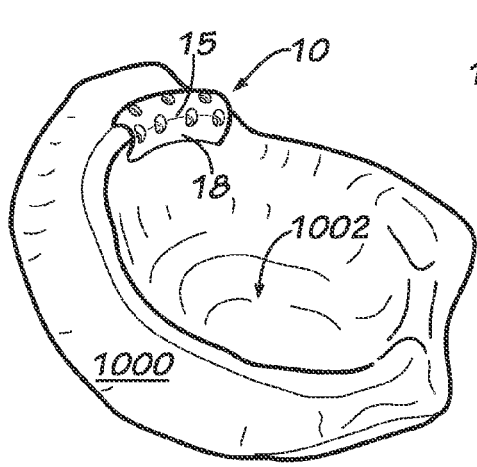
Figure 2F:
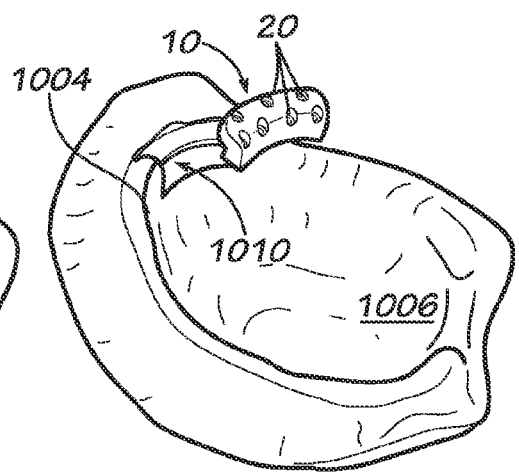

Various cutting inserts may be provided to fit within the insert aperture 162. For example, FIGS. 23A-B show a cutting insert 166 that includes a body portion 168 (defining a body cutting aperture 170) and a prong portion 172 (defining a prong cutting aperture 174). When inserted into the guide jig 150 (see FIG. 25), a shelf 180 on cutting insert 166 (shown in FIG. 23A) sits on top of the ledge 160 of the guide jig 150, and an extended portion 182 extends into the insert aperture 162. Other ways by which to ensure that the cutting insert 166 remains in the guide jig 150 are certainly contemplated herein. The prong cutting aperture 174 may be used as a template to cut, for example, prepared bone surface(s) 1011 shown in FIGS. 2B and 2D, and the body cutting aperture 170 may be used to cut prepared bone surface 1010. The cutting tool may be any type of tool known to one of skill in the art, such as a knife, a cutter, or a burr. If desired, the cutting tool may be provided with a guide bushing.

Figure 27:
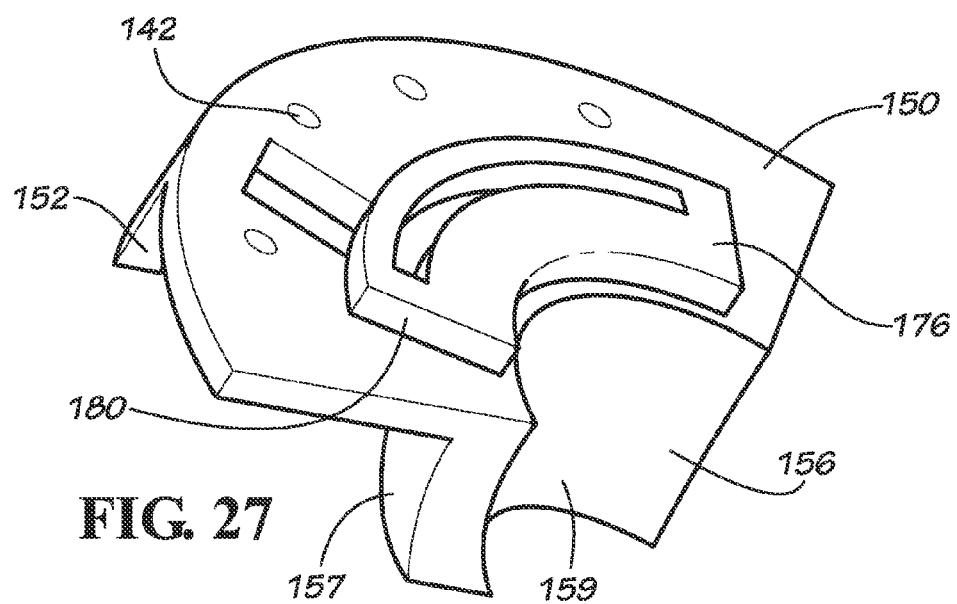
FIG. 27 is a top perspective view of the cutting insert of FIGS. 24A-B positioned in the guide jig of FIGS. 22A-E.

FIGS. 24A-B illustrate another embodiment of a cutting insert 176 that is received within insert aperture 162 of the guide jig 150, as shown in FIG. 27. The cutting insert 176 defines a body cutting aperture 178 that may be used as another template to prepare a bone surface. In the illustrated embodiments, body cutting aperture 178 of cutting insert 176 is narrower than body cutting aperture 170 of insert 166 and is located in a different position on cutting insert 176 than body cutting aperture 170 is located on cutting insert 166. Moreover, as shown in FIGS. 23A and 24A, the cutting inserts 166, 176 may have different thicknesses t1, t2. Thus, the geometry and features of the cutting inserts 166, 176 may differ, which provides for different shapes of prepared bone surfaces. Even more cutting inserts with different features may be provided to achieve different prepared bone surfaces.

Moreover, the specific geometry of the cutting inserts 166, 176 may be designed for a specific patient's anatomy and be based upon MRI or CT scans of the patient. Cutting inserts 166,176 may be coupled to the guide jug 150 either before or after the guide jig 150 is positioned on the acetabular rim.

Figure 28:
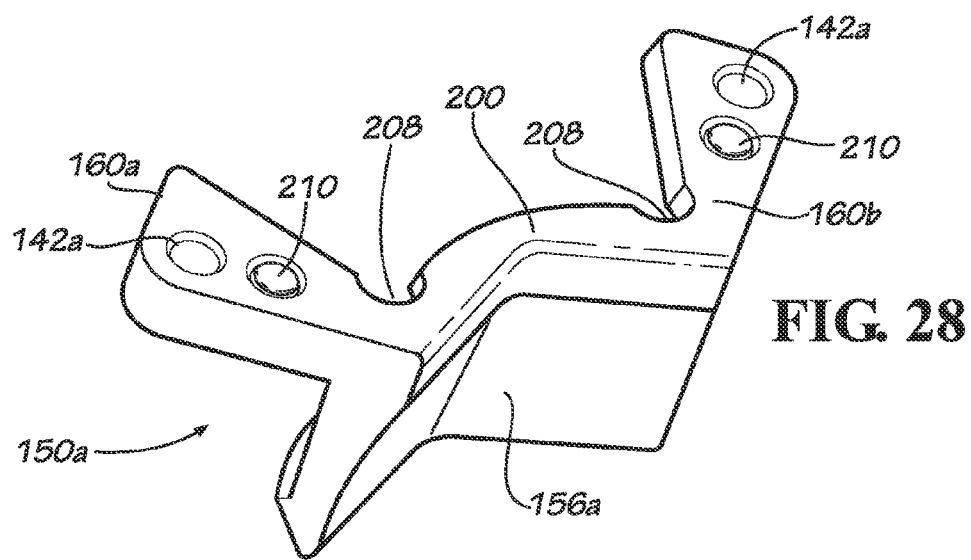
FIG. 28 is a top perspective view of a guide jig according to another embodiment.

FIG. 28 illustrates another embodiment of a guide jig 150a which is operationally very similar to guide jig 150 but includes structural differences which are highlighted here. The guide jig 150a includes two ledges 160a, 160b connected by a bridge 200 and a cup 156a (which can be, but does have to be, structurally similar to cup 156) that extends downwardly from the bridge 200. Stabilizing structure (such as lip 154 and tab 152 discussed above) may be provided on the underside of one or both ledges 160a, 160b. Fixation holes 142a may be provided in the ledges 160a, 160b to secure the guide jig 150a on the bone.

A cutting insert 202 (see FIGS. 29 and 30) is coupled to the guide jig 150a, as shown in FIG. 31. The cutting insert 202 may include any number of cutting apertures 204 having any geometry suitable to prepare a bone surface. In the disclosed embodiment, the cutting insert includes two alignment tongues 206, although any number of alignment tongues 206 may be provided. The guide jig 150a, in turn, includes two alignment grooves 208 that are sized and shaped to receive the alignment tongues 206. The cutting insert 202 is coupled to the guide jig 150a by inserting the alignment tongues 206 on the cutting insert 202 into the alignment grooves 208 on the guide jig 150a. Such engagement serves to ensure proper orientation of the cutting insert 202 on the guide jig 150a and prevent relative movement and rotation between the two. In other embodiments, the alignment tongues 206 are provided on the guide jig 150a and the alignment grooves 208 are provided on the cutting insert 202. Interaction between the alignment tongues 206 and alignment grooves 206 is but only one of a variety of ways to interlock the cutting insert 202 onto the guide jig 150a and this application is not intended to be limited only to the illustrated embodiment.

In certain embodiments, the cutting insert 202 may be further secured onto the guide jig 150a using magnets 210. In one such illustrative embodiment, magnets 210 are provided on ledges 160a, 160b of the guide jig 150a and provided on wings 212 of the cutting insert 202. When the cutting insert 202 is properly oriented and positioned on the guide jig 150a, the magnets 210 provided on the guide jig 150a align and mate with the magnets 210 provided on the cutting insert 202 to further reinforce the attachment of the cutting insert 202 on the guide jig 150a. Any number of magnets 210 may be provided and positioned in any location and by any means on the guide jig 150a and cutting insert 202. In certain embodiments, magnets 210 are positioned within recesses 210 provided on the guide jig 150a and the cutting insert 202. In other embodiments, adhesive is used to sure the magnets 210 to the guide jig 150a and the cutting insert 202.

In use, the cup 156a of the guide jig 150a is inserted against the acetabulum 1002 and the ledges 160a, 160b extend over the acetabular rim 1004. The cup 156a may receive the patient's femoral head 1014 (and may distract the femoral head 1014 from the acetabulum 1002). The guide jig 150a may be secured to the bone by inserting anchors into fixation holes 142a located on ledges 160a, 160b. A cutting insert 202 having the appropriate cutting aperture 204 geometry is selected and removably mated with the guide jig 150a as discussed above. The cutting aperture 204 may be used as a template to remove the underlying bone.

The guide jigs 150, 150a and cutting inserts 166, 176, 202 may be made from any material, including, but not limited to, any material identified in this disclosure.

Embodiments of the guide jig 150, 150a and cutting inserts 166, 176, 202 are modular in design such that the surgeon may select the particular cutting insert 166, 176, 202 (or multiple inserts) needed to customize and prepare a bone surface for a particular patient and easily swap out cutting inserts as needed. Embodiments provide for intraoperative flexibility in that a different cutting insert 166, 176, 202 may be selected based on new information learned during surgery. Embodiments also provide for reduced manufacturing costs, because a single guide jig 150, 150a may accommodate a variety of different cutting inserts 166, 176, 202 (which are less expensive to manufacture than a guide jig 150, 150a).

The foregoing is provided for purposes of illustrating, explaining, and describing embodiments of the present invention. Further modifications and adaptations to these embodiments will be apparent to those skilled in the art and may be made without departing from the scope or spirit of the invention. Different arrangements of the components depicted in the drawings or described above, as well as components and steps not shown or described are possible. Similarly, some features and subcombinations are useful and may be employed without reference to other features and subcombinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications can be made without departing from the scope of the claims below.

We claim:

1. A system for guiding removal of bone along an acetabular rim of an acetabulum, the system comprising:
   a. a guide jig comprising a first ledge and a second ledge connected to the first ledge, wherein the first ledge and the second ledge are adapted to extend over the acetabular rim, and a cup connected to the first ledge and the second ledge and adapted to be positioned within the acetabulum; and
   b. at least one cutting insert defining a cutting aperture and removably mountable on the guide jig
   wherein the at least one cutting insert comprises a plurality of cutting inserts, each cutting insert defining a cutting aperture geometry, wherein the geometry of at least some of the cutting apertures of at least some of the plurality of cutting inserts is different.

2. The system of claim 1, wherein at least one of the guide jig or at least one of the plurality of cutting inserts comprises an alignment tongue and the other of the guide jig or the at least one of the plurality of cutting inserts comprises an alignment groove adapted to receive the alignment tongue.

3. The system of claim 1, wherein at least one magnet is provided on the guide jig and wherein at least one magnet is provided on at least one of the plurality of cutting inserts, wherein the at least one magnet on the guide jig and the at least one magnet on the at least one of the plurality of cutting inserts align when the at least one of the plurality of cutting inserts is mounted properly on the guide jig.

4. The system of claim 1, wherein the cup extends downwardly from the first and second ledges.

5. The system of claim 1, wherein the inner surface of the cup and an outer surface of the cup opposite the inner surface of the cup are both curved.

6. The system of claim 1, wherein the cup further comprises an outer surface on a side of the guide jig opposite the inner surface of the cup, and wherein the first and second ledges extend away from the inner surface of the cup, on the same side as the outer surface of the cup.

7. The system of claim 1, wherein at least one of the cutting apertures includes an elongated and curved template portion.

8. The system of claim 1, wherein the cutting aperture geometry of at least one of the plurality of cutting inserts includes an elongated and curved template portion configured to guide the formation of an elongated and curved bone surface along the acetabular rim.

9. A system for guiding removal of bone along an acetabular rim of an acetabulum, the system comprising:
   a. a guide jig comprising a first ledge and a second ledge connected to the first ledge, wherein the first ledge and the second ledge are configured to extend over the acetabular rim, and a cup connected to the first ledge and the second ledge, extending downwardly from the first and second ledges, and configured to extend into the acetabulum, wherein the cup includes an inner surface defining a hollow shaped to receive a femoral head; and
   b. at least one cutting insert defining a cutting aperture and removably mountable on the guide jig
   wherein the cutting aperture of the cutting insert includes an elongated and curved template portion configured to guide the formation of an elongated and curved bone surface along the acetabular rim.

10. The system of claim 9, wherein the cup includes an outer surface opposite the inner surface, wherein the outer surface is shaped to interact with the acetabulum.

11. The system of claim 10, wherein the outer and inner surfaces of the cup are curved.

12. The system of claim 9, wherein the first and second ledges are connected by a bridge.

13. The system of claim 12, wherein the cup is connected to the bridge and extends downwardly therefrom.

14. A system for guiding removal of bone along an acetabular rim of an acetabulum, the system comprising:
   a. a guide jig comprising: (i) at least two ledge portions configured to extend over the acetabular rim, and (ii) a cup extending downwardly from the two ledge portions and configured to extend into the acetabulum, wherein the cup includes an inner surface defining a hollow configured to receive a femoral head and an outer surface opposite the inner surface configured to abut the acetabulum;
   b. a first cutting insert defining a first cutting aperture including a first curved and elongated geometry, the first cutting insert including first alignment structure configured to removably interlock the first cutting insert to the ledge portions and prevent relative movement and rotation between the first cutting insert and the guide jig; and
   c. a second cutting insert defining a second cutting aperture including a second curved and elongated geometry that is different from the first curved and elongated geometry, the second cutting insert including second alignment structure configured to removably interlock the second cutting insert to the ledge portions and prevent relative movement and rotation between the second cutting insert and the guide jig.

15. The system of claim 14, wherein the inner and outer surfaces of the cup are curved.

16. The system of claim 14, wherein the two ledge portions are connected by a bridge.

17. The system of claim 16, wherein, when the first cutting insert is removably interlocked to the ledge portions, the ledge portions and the bridge are on three sides of the first cutting insert.

18. The system of claim 16, wherein the cup is connected to the bridge and extends downwardly therefrom.

* * * * *